(12) United States Patent
Milojevic et al.

(10) Patent No.: US 8,538,541 B2
(45) Date of Patent: Sep. 17, 2013

(54) SUBTHRESHOLD STIMULATION OF A COCHLEA

(75) Inventors: Dusan Milojevic, Westleigh (AU); John Parker, Roseville (AU)

(73) Assignee: Cochlear Limited, Macquarie University, NSW (AU)

( * ) Notice: Subject to any disclaimer, the term of this patent is extended or adjusted under 35 U.S.C. 154(b) by 2510 days.

(21) Appl. No.: 10/494,995

(22) PCT Filed: Nov. 11, 2002

(86) PCT No.: PCT/AU02/01537
§ 371 (c)(1),
(2), (4) Date: Sep. 23, 2004

(87) PCT Pub. No.: WO01/43818
PCT Pub. Date: Jun. 21, 2001

(65) Prior Publication Data
US 2005/0033377 A1    Feb. 10, 2005

(30) Foreign Application Priority Data

Nov. 9, 2001 (AU) ............................................ 8792

(51) Int. Cl.
*A61N 1/00* (2006.01)
(52) U.S. Cl.
USPC .......................................................... 607/57
(58) Field of Classification Search
USPC .......................................................... 607/57
See application file for complete search history.

(56) References Cited

U.S. PATENT DOCUMENTS

| | | |
|---|---|---|
| 4,063,048 A | 12/1977 | Kissiah, Jr. |
| 4,357,497 A | 11/1982 | Hochmair et al. |
| 4,506,680 A | 3/1985 | Stokes |
| 4,532,930 A | 8/1985 | Crosby et al. |
| 4,611,596 A * | 9/1986 | Wasserman ..................... 607/57 |
| 4,784,161 A | 11/1988 | Skalsky et al. |
| 4,819,662 A | 4/1989 | Heil, Jr. et al. |
| 4,844,099 A | 7/1989 | Skalsky et al. |
| 4,972,848 A | 11/1990 | Di Domenico et al. |
| 5,066,278 A | 11/1991 | Hirschberg et al. |
| 5,092,332 A | 3/1992 | Lee et al. |
| 5,095,904 A | 3/1992 | Seligman et al. |

(Continued)

FOREIGN PATENT DOCUMENTS

| DE | 100 32 0000 A1 | 1/2001 |
|---|---|---|
| JP | 2005-507746 A | 3/2005 |

(Continued)

OTHER PUBLICATIONS

Written Opinion, PCT/AU02/01537, mailed Jun. 23, 2003.

(Continued)

*Primary Examiner* — George Manuel
(74) *Attorney, Agent, or Firm* — Kilpatrick, Townsend & Stockton, LLP.

(57) ABSTRACT

An implantable apparatus, such as a cochlear implant, for delivering electrical plasticity informative stimuli to a neural network of an implantee. The apparatus comprises a stimulator device (40) that generates stimulation signals, and an electrode array (20) that receives the stimulation signals and delivers the stimuli to the neural network of the implantee in response to the signals. The stimuli delivered to the implantee facilitates and/or controls the production and/or release of naturally occurring agents into the neural network to influence the functionality thereof.

113 Claims, 7 Drawing Sheets

(56) References Cited

U.S. PATENT DOCUMENTS

| | | | |
|---|---|---|---|
| 5,262,608 A | 11/1993 | Mustonen | |
| 5,458,631 A | 10/1995 | Xavier | |
| 5,531,780 A | 7/1996 | Vachon | |
| 5,611,350 A * | 3/1997 | John | 600/378 |
| 5,653,742 A | 8/1997 | Parker et al. | |
| 5,697,951 A | 12/1997 | Harpstead et al. | |
| 5,755,474 A | 5/1998 | Slomski | |
| 5,792,751 A * | 8/1998 | Ledley et al. | 514/44 |
| 5,929,041 A | 7/1999 | Magal | |
| 5,941,906 A | 8/1999 | Barreras, Sr. et al. | |
| 5,975,085 A | 11/1999 | Rise | |
| 6,038,482 A | 3/2000 | Vachon | |
| 6,038,484 A | 3/2000 | Kuzma | |
| 6,043,221 A * | 3/2000 | Magal et al. | 514/12 |
| 6,078,841 A | 6/2000 | Kuzma | |
| 6,121,235 A * | 9/2000 | Gao | 514/12 |
| 6,125,302 A | 9/2000 | Kuzma | |
| 6,129,685 A | 10/2000 | Howard, III | |
| 6,163,729 A | 12/2000 | Kuzma | |
| 6,175,767 B1 | 1/2001 | Doyle, Sr. | |
| 6,221,908 B1 * | 4/2001 | Kilgard et al. | 514/546 |
| 6,249,704 B1 * | 6/2001 | Maltan et al. | 607/57 |
| 6,259,951 B1 | 7/2001 | Kuzma et al. | |
| 6,304,787 B1 | 10/2001 | Kuzma et al. | |
| 6,309,410 B1 | 10/2001 | Kuzma et al. | |
| 6,321,125 B1 | 11/2001 | Kuzma | |
| 6,331,537 B1 * | 12/2001 | Hamilton et al. | 514/215 |
| 6,429,191 B1 * | 8/2002 | Gao | 514/2 |
| 6,429,196 B1 * | 8/2002 | Gao | 514/12 |
| 6,565,503 B2 | 5/2003 | Leysieffer et al. | |
| 6,649,621 B2 * | 11/2003 | Kopke et al. | 514/266.1 |
| 6,671,559 B2 * | 12/2003 | Goldsmith et al. | 607/57 |
| 6,936,040 B2 | 8/2005 | Kramm et al. | |
| 7,044,942 B2 | 5/2006 | Jolly et al. | |
| 7,206,639 B2 | 4/2007 | Jacobsen et al. | |
| 2002/0032477 A1 | 3/2002 | Helmus et al. | |
| 2002/0115706 A1 * | 8/2002 | Ylikoski et al. | 514/410 |
| 2002/0176859 A1 | 11/2002 | Gao | |
| 2003/0171787 A1 | 9/2003 | Money et al. | |
| 2004/0082980 A1 * | 4/2004 | Mouine et al. | 607/48 |
| 2004/0122475 A1 | 6/2004 | Myrick et al. | |
| 2004/0247570 A1 | 12/2004 | Miller et al. | |
| 2005/0171579 A1 | 8/2005 | Tasche et al. | |
| 2005/0256560 A1 * | 11/2005 | Lenarz et al. | 607/137 |
| 2006/0171922 A1 * | 8/2006 | Federoff et al. | 424/93.2 |
| 2008/0033520 A1 | 2/2008 | Jolly | |
| 2009/0062896 A1 | 3/2009 | Overstreet et al. | |
| 2009/0292237 A1 | 11/2009 | Overstreet et al. | |
| 2010/0030130 A1 | 2/2010 | Parker et al. | |

FOREIGN PATENT DOCUMENTS

| | | |
|---|---|---|
| JP | 2008-528190 A | 7/2008 |
| WO | 97/10784 A1 | 3/1997 |
| WO | 99/00067 A1 | 1/1999 |
| WO | 99/55360 A1 | 11/1999 |
| WO | 00/57949 A1 | 10/2000 |
| WO | 00/71063 A1 | 11/2000 |
| WO | 01/41674 A1 | 6/2001 |
| WO | 01/41867 A1 | 6/2001 |
| WO | WO 01/43818 | 6/2001 |
| WO | WO 01/43818 A1 | 8/2001 |
| WO | 01/97908 A2 | 12/2001 |
| WO | 02/24064 A1 | 3/2002 |
| WO | 02/32498 A1 | 4/2002 |
| WO | 02/41666 A1 | 5/2002 |
| WO | 02/55136 A2 | 7/2002 |
| WO | 02/83234 A1 | 10/2002 |
| WO | 02/087681 A2 | 11/2002 |
| WO | 03/039660 A1 | 5/2003 |
| WO | 03/049658 A1 | 6/2003 |
| WO | 03/072193 A1 | 9/2003 |
| WO | 2009/124041 A1 | 10/2009 |
| WO | 2010/045432 A2 | 4/2010 |

OTHER PUBLICATIONS

International Preliminary Examination Report, PCT/AU02/01537, dated Feb. 13, 2004.
International Search Report. PCT/US06/02793. Mailed May 10, 2007.
Altschuler, et al., "Rescue and Regrowth of Sensory Nerves Following Deafferentation by Neurotrophic Factors", Annals New York Academy of Sciences, Nov. 28, 1999, pp. 305-311.
Australian Application No. 2002223270, First Examination Report mailed on Aug. 17, 2005.
Australian Application No. 2003283124, First Examination Report mailed on Jun. 13, 2008.
Australian Application No. 2006211170, Office Action mailed on Aug. 4, 2010, 6 Pages.
Canadian Application No. 2,428,542, Office Action mailed on May 15, 2009.
European Application No. 01994538, Examination Report mailed on Apr. 20, 2007, 4 Pages.
European Application No. 01994538, Supplementary European Search Report mailed on May 27, 2005, 3 Pages.
European Application No. 03702212, Examination Report mailed on Aug. 7, 2008, 5 Pages.
European Application No. 03702212, Supplementary Partial European Search Report mailed on Jun. 23, 2006, 4 Pages.
European Application No. 02774174.3, Office Action mailed on Jul. 13, 2011, 6 Pages.
European Application No. 02774174.3, Supplementary European Search Report mailed on Mar. 11, 2011, 3 Pages.
Japanese Application No. 2007-553227, Office Action mailed on Feb. 22, 2011, 6 Pages.
International Application No. PCT/AU2001/001479, International Preliminary Examination Report mailed on May 14, 2003, 10 Pages.
International Application No. PCT/AU2001/001479, International Search Report mailed on Dec. 3, 2001, 3 Pages.
International Application No. PCT/AU2001/001479, Written Opinion of the International Searching Authority mailed on Jan. 28, 2002.
International Application No. PCT/AU2003/000248, International Preliminary Examination Report mailed on Jun. 2, 2004, 4 Pages.
International Application No. PCT/AU2003/000248, International Search Report mailed on Apr. 7, 2003, 3 Pages.
International Application No. PCT/AU2003/001584, AT 2nd Office Action and English Translation mailed on Mar. 20, 2007.
International Application No. PCT/AU2003/001584, International Preliminary Examination Report mailed on Mar. 15, 2005, 6 Pages.
International Application No. PCT/AU2003/001584, International Search Report mailed on Apr. 2, 2004, 3 Pages.
International Application No. PCT/US2009/038942, International Search Report mailed on May 28, 2009, 13 Pages.
International Application No. PCT/AU02/01537, Written Opinion mailed on Jun. 23, 2003.
International Application No. PCT/AU02/01537, International Preliminary Examination Report mailed on Feb. 13, 2004.
International Application No. PCT/AU02/01537, International Search Report mailed on May 10, 2007.
Mitchell et al., "Effects of chronic high-rate electrical stimulation on the cochlea and eighth nerve in the guinea pig" Hearing Research, Elsevier Science Publishers, Amsterdam, NL, vol. 105, No. 1-2, Mar. 1997, p. 30-43, XP009094144.

* cited by examiner

SUBTHRESHOLD STIMULATION OF A COCHLEA

CROSS REFERENCE TO RELATED APPLICATIONS

This application claims the priority of and is a national stage application of PCT Application No. PCT/AU02/01537, entitled, "Subthreshold Stimulation of a Cochlea," filed on Nov. 11, 2002, which claims the priority of Australian Provisional Application No. PR 8797, filed on Nov. 9, 2001. The entire contents and disclosures of the above applications are hereby incorporated by reference.

FIELD OF THE INVENTION

The present invention relates to an implantable apparatus for delivering electrical stimulation to at least a portion of a neural network of a nervous system of the implantee, and, in particular, for the purpose of facilitating and controlling the production and/or release of naturally occurring agents into the neural network to influence and control the functionality of the neural network. The functionality may include but is not limited to neural plasticity, outgrowth of neurons and the neural firing threshold.

BACKGROUND OF THE INVENTION

The human nervous systems, both central and peripheral, are dynamic entities. One way this dynamic nature of both nervous systems is expressed is a constant change in the way neurons are connected or arranged to allow communication therebetween. Communication in the nervous system includes signalling or information transfer within and between the neurons. The structure of a neuron is unique and reflects this essential function of the nervous system. In addition to the neuron cell body, called the soma, which is structurally similar to other biological cells, the neuron also features two characteristic structural elements that are essential for the signalling process, namely the axon and the dendrite.

The axon is a cell structure specialised for intracellular transfer of information over long distances. An axon originates at a cone-shaped thickening on the cell body called the axon hillock. Information is transmitted within neurons via electrical signals. Such electrical signals are represented by the action potential, which is a single, transient reversal of membrane polarity. The action potential is the basic unit of signalling in the neural system. The intracellular information transfer is carried out by conduction of the action potential along the axon and this conducting mechanism is known as saltatory conduction.

The synaptic terminal is situated at the opposite end of the axon. The synaptic terminal contains synaptic vesicles, which play an important role in interneural communication.

Many, but not all, axons in a vertebrate nervous system are surrounded by a myelin sheath. This sheath is formed by oligodendrocytes on central nervous system axons and by Schwann cells in the peripheral nervous system. The sheath is not a continuous structure but features gaps several microns wide. These gaps are known as the nodes of Ranvier and play an important role in intraneural transport of information.

The dendrite is a cell structure specialised to receive information from other neurons. Dendrites, in general, are shorter than axons, frequently highly branched, and form a dense network known as a dendritic tree.

Another important structural entity necessary for signalling is the synapse. The synapse is a highly specialised structure that mediates the transfer of information from one neuron to another. In general, the term synapse refers to the junction where communication occurs between two excitable cells, e.g. neuron and neuron, or neuron and muscle cell. Synapses and synaptic transmission can be electrical and chemical, depending on the nature of the information transfer.

In a typical chemical synapse, a branch of the afferent or presynaptic axon swells at its terminus to form a bouton, which is very close to, but does not actually physically touch the specialised postsynaptic side of the synapse. Most neurons have a dendrite that is capable of responding to a chemical signal transmitted from the presynaptic axon. The gap between the two communicating neurons is typically 20 nm wide and is called the synaptic cleft. The fluid-filled gap between the two neurons prevents the direct transfer of electrical current from one neuron to another. The signal transfer between the neurons is instead carried out by rapid diffusion of naturally occurring chemicals called neurotransmitters. The molecules comprising the neurotransmitters in a presynaptic neuron are contained within synaptic vesicles. The signal transmission occurs by synaptic vesicles fusing with the cell membrane of the presynaptic neuron, excreting the neurotransmitters molecules to the cleft which than rapidly diffuse and interact with the postsynaptic neuron where it may produce either an excitatory or inhibitory postsynaptic potential.

Frequently, the number of neurons that sense information about an environment is measured in the thousands and this information, collected by a large number of sensors, is imported into the brain for processing. Whilst information between two neurons is still transmitted through the synapse, a network of interacting cells is required for the full spectrum of information to be collected and transferred to the brain.

Signalling is essential for an organism if it wishes to:
1. Sense information about an environment;
2. Import that information into its brain where it can be processed; and
3. Generate a behavioural response.

Neural rearrangements are a necessary part of a normal developmental process. However, neural rearrangements may also occur as an organism's response to events that inhibit natural functionality. For example, functional and structural changes in the auditory system of a person may effect the way that person perceives sound and may even deprive them from receiving sound at all. Frequently though, even though there are substantial changes in functionality of the auditory system, such as sensorineural loss of hearing, organisation of the auditory system is maintained.

The auditory system can be divided into two large subsystems, namely the peripheral auditory system and the central auditory system.

The peripheral auditory system converts the condensation and rarefaction of air that produces sound into neural codes that are interpreted by the central auditory system as specific sound tokens.

The peripheral auditory system is subdivided into the external ear, the middle ear, and the inner ear. The external ear collects the sound energy as pressure waves which are converted to mechanical motion of the eardrum. This motion is transformed across the middle ear and transferred to the inner ear, where it is frequency analysed and converted into neural codes that are carried by the eighth cranial nerve, ie. the auditory nerve, to the central auditory system.

Sound information, encoded as discharges in an array of thousands of auditory nerve fibers, is processed in nuclei that make up the central auditory system. The major centers include the cochlear nuclei (CN), the superior olivary complex (SOC), the nuclei of the lateral leminiscus (NLL), the inferior colliculi (IC), the medial geniculate body (MGB) of the thalamus, and the auditory cortex (AC). The CN, SOC, and NLL are brainstem nuclei, while the IC is at the midbrain level and the MGB and AC constitute the auditory thalamo-cortical system.

Sound, in a form of a mechanical wave, enters the cochlea at the round window. The cochlea is filled with fluid and the mechanical wave travels firstly through the scala vestibuli upwardly towards the apical part of the cochlea. At the very top of the cochlea, the scala vestibule and scala tympani connect through the helicotrema. As the mechanical wave travels downwardly through the scala tympani it initiates displacement in the basilar membrane. This motion has frequency-dependent characteristics which arise from properties of the membrane and surrounding structures.

Displacement of the basilar membrane is sensed by the inner hair cells, through a mechanism involving the Organ of Corti, and at this point the mechanical signal is encoded to an electrical signal. Such an electrical signal is then transferred through radial fibers to the spiral ganglion cells.

The electrical signal is further transmitted to the cochlear nucleus, which is the first obligatory synapse in the ascending auditory path, and then further as described previously. The frequency-dependant characteristics of the basilar membrane are reflected in the fact that the membrane is more responsive to low frequency sound at the apical end of the cochlea, and to high frequency sound at the basal end of the cochlea. In general, such frequency or tonotopic organisation of the basilar membrane is transferred to the hair cells and to the rest of the auditory system. The auditory system is organised tonotopically, ie. in order of frequency, because the frequency ordering of the cochlea is mapped through successive levels of the system.

This tonotopic organisation of the auditory system can be represented by threshold curves which are also called tuning curves. The threshold tuning curves for axons in the auditory nerve show a minimal threshold (maximum sensitivity) at a characteristic frequency with a narrow frequency range of responding for slightly more intense sounds. A threshold level can be identified as a minimum intensity that would evoke a discharge rate significantly higher than the spontaneous discharge rate. The threshold or neural tuning curve is not to be confused with the mechanical tuning curve which shows how the stimulus intensity must be changed relative to frequency so that a particular point on the basilar membrane always has the same deflection amplitude. The width of the tuning curves can be used as a measure of selectivity, or ability to discriminate between sounds.

Further, the auditory system is designed to accept signals from two independent sources, ie. two ears. The normal existence of two independent inputs has an important role in a number of processes such as sound localisation.

An apparatus for delivering random patterns of activation to the auditory nerve to generate psuedospontaneous activity in the nerve is described in U.S. Pat. No. 6,295,472. While this system is described as useful for treating tinnitus, the patent does not describe use of an apparatus that delivers stimulation in a manner that controls the production and/or release of naturally occurring agents into the auditory system.

In recent times, a high degree of hearing loss in both ears (profound loss of hearing) has been successfully treated with a cochlear implant.

Successful use of a cochlear implant rests with the fact that the spiral ganglion cells (SGC) and the rest of the auditory system through to the auditory cortex are still fully functional in the implantee. It is important to note that the cochlear implant does not restore the function of damaged (ie. non-functional) parts of the auditory system, primarily the inner hair cells, but actually presents spiral ganglion neurons with electrical activity that in normal hearing subjects is generated by the hair cells and transferred by the radial fibres to the spiral ganglion cells.

The cochlear implant analyses sound and encodes it in a train of electrical pulses that stimulate the auditory nerve fibres. The train of pulses carry both frequency and time information. All currently available cochlear implants achieve this task through stimulation of nerve fibres by activation of multiple stimulating electrodes located on a flexible carrier inserted in the cochlea. Successful use of a cochlear implant is associated with a habituation process during which a cochlear implant user learns to interpret electrical signals presented by the implant as meaningful sound.

As a result of the presented electrical stimulation to the SGC, major changes in the auditory system of the implantee may occur. The cochlear implant is generally implanted in only one ear, resulting in stimulus coming from one source instead of two source. Secondly, even the presently most advanced cochlear implants only have a very limited number of stimulating pads, typically between 6 and 22 electrodes. This is in contrast to normal hearing people where the received auditory stimulus is processed by between 3000-4000 hair cells.

As a result of facilitated activity of the SGC in one cochlea only and stimulation through a very limited number of stimulating electrodes, the neural paths that transport signal from the SGC to the auditory cortex may undergo rearrangements with certain synapses disappearing and other completely new synapses being formed to reflect the patterns of neural activity. Such rearrangement of the neural path is essentially uncontrolled and normal use of a cochlear implant does not provide any mechanism for the controlled modification of the neural paths of the implantee.

The efficiency and potential benefits that the cochlear implant may provide heavily depend on the plasticity of the neural system of the implantee. For example, it is well known that efficiency of the implant decreases as the length of deafness, particularly in prelingually deaf people, increases.

Some other examples where neural rearrangements occur as a consequence of an injury or treatment of the injury include, but are not limited to, visual impairment, sensorineural and motorneural injuries. Further, the device may be used to treat abnormal functionality of part of a neural system. Sensorineural and motorneural abnormalities, such as depression, Parkinson's disease, Alzheimer's disease may also be treated with the herein described device. These diseases may be treated at present with naturally occurring agents, administered to a patient through a mechanism(s) other than electrical stimulation, e.g. oral administration of agents in a form of a tablet.

The present invention is in part directed to an apparatus that is adapted to improve or maintain the plasticity of the neural system of a patient with a cochlear implant.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

According to one aspect, the present invention is an implantable apparatus for delivering electrical stimuli to a neural network of an implantee, the apparatus comprising:

a stimulator device that generates stimulation signals; and at least one electrode member that receives the stimulation signals and delivers said stimuli to the neural network in response to said signals;

wherein the stimuli facilitates and/or controls the production and/or release of naturally occurring agents into the neural network to influence the functionality thereof.

In a further aspect, the present invention is an implantable apparatus for making desired modifications to the functionality of a neural network of an implantee, the apparatus comprising:

a stimulator device that generates stimulation signals; and at least one electrode member that receives the stimulation signals and delivers said stimuli to the neural network in response to said signals;

wherein the stimuli facilitates and/or controls the production and/or release of naturally occurring agents into the neural network to influence the functionality thereof.

As used herein, the term "neural network" is to be understood as including the entire nervous system of the implantee, including the peripheral and central nervous systems.

In a preferred embodiment, the stimuli modifies the functionality of the neural network in a predetermined desired manner. In particular, the present invention preferably provides an apparatus that can make controlled rearrangement of the neural network.

In a preferred embodiment, the apparatus is adapted to deliver stimuli to the auditory system of the implantee. The stimuli can be delivered to the cochlea, (e.g. via intracochlear electrode or endosteal electrode), cochlear nucleus (e.g. via an auditory brainstem implant (ABI) or PABI electrode), inferior colliculus (e.g. via MBI electrode) or any other part of the auditory system. Further, stimulation can be delivered to the Subthalamic Nucleus (STN), the Globus Pallidus (GPi), and/or the Thalamus of the implantee. Such stimulation would be administered via deep brain stimulation.

The stimuli delivered by the apparatus can comprise plasticity informative stimuli having a magnitude below the auditory perception threshold of the implantee.

In a still further embodiment, the apparatus can be a component of a hearing prosthesis that is also adapted to deliver auditory informative stimuli having a magnitude that is about at or above the auditory perception threshold of the implantee to the auditory system of the implantee.

The hearing prosthesis can be a cochlear implant, a middle ear implant, or a hearing aid.

The cochlear implant can include an electrode array that is implantable in the cochlea of the implantee and which is adapted to deliver both plasticity informative stimuli and auditory informative stimuli to the cochlea of the implantee.

Further, the hearing prosthesis could be a cochlear implant having an endosteal electrode array, which is not inserted into the scala tympani, but rather into a natural crevice in the cochlea that allows for the hydrodynamic nature of the cochlea to be maintained. Still further, the hearing prosthesis could be an Auditory Brainstem Implant (ABI) whereby the stimulating electrodes are not inserted into the cochlea but are positioned adjacent the cochlear nucleus. Still further, the hearing prosthesis could be a MidBrain Implant (MBI) wherein the stimulating electrode is positioned adjacent the inferior colliculus to apply the appropriate stimulus.

In one embodiment, the prosthesis can comprise a first electrode array for delivering plasticity informative stimuli and a second electrode array for delivering auditory informative stimuli to the auditory system of the implantee.

In this regard, the first electrode array can be insertable into the neural network at a location different from that of the second electrode array.

In a further embodiment, both said first and said second electrode arrays can comprise an elongate carrier member having a plurality of electrodes mounted thereon. The stimulator device can be electrically connected to each of the elongate carrier members by way of an electrical lead, the lead including one or more wires extending from each electrode of each elongate member.

In a still further embodiment, the hearing prosthesis can include an external component that works in conjunction with the implantable apparatus, the external component comprising:

a microphone that detects sounds and outputs acoustic signals representative of said detected sounds;

a processor that receives said acoustic signals from the microphone and converts the signals into stimulation signals representative of the detected sounds that are then delivered transcutaneously to the stimulator device.

In this embodiment, the external component can also comprise a controller that controls the output of the stimulator device. Still further, the external component can comprise a power source. The controller can control the type of stimuli output by the stimulator device. It can also control when a particular type of stimuli is delivered by the stimuli device to the electrode. It can also control the features of the stimuli (eg. the magnitude of the stimuli, the rate of repetition of the stimuli, the period of time between each stimuli, and even which electrode of said at least one electrode receives the output of the stimulator device).

In yet another embodiment, the apparatus can be adapted to deliver plasticity informative stimuli to the cochlea of an implantee and work in conjunction with a cochlear implant device or any other hearing assistant device adapted to deliver auditory informative stimuli to the same cochlea of the implantee. In this embodiment, the apparatus can be housed in a different housing to that of the implantable component of the cochlear implant.

In a still further embodiment, the implantable apparatus can work in conjunction with an external component, the external component comprising a controller that controls the output of the plasticity informative stimuli from the stimulator device. In this embodiment, the external component can further comprise a power source. The power source can comprise one or more rechargeable batteries. In this embodiment, the apparatus can be adapted to only be capable of delivering plasticity informative stimuli.

In another embodiment, the stimulator device can be housed in a housing that is totally implantable within the implantee. In this case, the housing can further house a power source that provides the apparatus with at least sufficient power to deliver plasticity informative stimuli.

In a still further embodiment, the at least one electrode member can be part of an electrode array that is implantable in the auditory system of the implantee. In this embodiment, the electrode array can comprise an elongate electrode carrier member having a plurality of electrodes mounted thereon. The stimulator device can be electrically connected to the elongate member by way of an electrical lead, the lead including one or more wires extending from each electrode of the array mounted on the elongate member.

In one embodiment, the apparatus can comprise a cochlear implant that is adapted to deliver electrical stimulation to the cochlea of an implantee and preferably, the basilar membrane of the cochlea. A more detailed description of the cochlear implant is provided below.

The application of the apparatus is, however, not limited to the auditory system and can be successfully used to treat other conditions caused by the lack of natural functionality or abnormal function. For example, spinal cord injury, visual impairment, sensorineural and motorneural abnormalities, such as depression, Parkinson's disease, Alzheimer's disease may also be treated with the herein described device.

To treat problems with the visual system, stimulus can be delivered to the retina or visual cortex, in patients suffering from loss of vision. In this regard, retinal and visual cortex implants are the two most commonly investigated devices for applying such stimulation for the visually impaired. In this embodiment, the apparatus can be adapted to solely deliver plasticity informative stimuli to the visual system of the implantee.

For the treatment of spinal cord injured patients, the stimulus can be delivered to various locations along the patient's spinal cord.

When the apparatus is delivering stimuli to the cochlea, the electrical stimulation can have a magnitude less than the auditory perception threshold of the implantee that is hereinafter termed "plasticity informative stimuli" or a magnitude about equal to or greater than the auditory perception threshold of the implantee that is hereinafter termed "auditory informative stimuli". The apparatus can be adapted to deliver both types of stimuli to the implantee.

Similarly, when the apparatus is delivering stimuli to the visual system, the electrical stimulation can have a magnitude less than the visual perception threshold of the implantee that is hereinafter termed "plasticity informative stimuli" or a magnitude about equal to or greater than the visual perception threshold of the implantee that is hereinafter termed "visual informative stimuli". The apparatus can be adapted to deliver both types of stimuli to the implantee.

In another embodiment, the apparatus can be adapted to solely deliver plasticity informative stimuli to the cochlea of the implantee.

In another embodiment, the apparatus can be adapted to solely deliver plasticity informative stimuli to the visual system of the implantee.

The plasticity informative stimuli once delivered to the cochlea is transmitted through the central auditory system of the implantee, including the cochlear nuclei (CN), the superior olivary complex (SOC), the nuclei of the lateral leminiscus (NLL), the inferior colliculi (IC), the medial geniculate body (MGB) of the thalamus, and the auditory cortex (AC). Similarly, if the plasticity informative signal is delivered higher up in the system, e.g. at the level of CN (via an ABI) or IC (via an MBI), the plasticity informative signal may be transmitted through the structures of the auditory system positioned above the place of stimulation. As described above, the CN, SOC, and NLL are brainstem nuclei, while the IC is at the midbrain level, and the MGB and AC constitute the auditory thalamocortical system.

Delivery of such plasticity informative stimuli preferably results in the production and release of said naturally occurring agents into the neural network to influence, and more preferably control, the functionality thereof.

In one embodiment, said naturally occurring agents can comprise one or more neurotrophic factors or neurotrophins.

In one embodiment, one of the neurotrophic factors can comprise Brain Derived Neurotrophic Factor (BDNF).

In another embodiment, the neurotrophic factors can be selected from the group comprising, but not limited to, NGF, NT-3, NT4/5, NT-6, LIF, GDNF, CNTF, and IGF-1.

In another embodiment, the said naturally occurring agents can comprise one of more factors, other then neurotrophins, which have a capacity to activate the neurotrophic receptors, for example adenosine, a neuromodulator.

Neurotrophic factors produce their effects on neurons by binding to neurotrophic receptors, such as trk receptors and a glucoprotein termed p75. The receptors span the plasma membrane. The extracellular part of the receptor molecule contains binding sites for neurotrophins. The intracellular part of the receptor features an enzyme active structural element, ie. a tyrosine kinase. There are three known trk proteins, termed trkA, trkB and trkC that preferentially bind NGF, BDNF and NT-4/5, and NT-3, retrospectively. It is generally assumed that neurotrophins are synthesised and packaged into vesicles in the soma in direct proportion to its mRNA, and that they are then transported to either presynaptic axon terminals or postsynaptic dendrites for local secretion. The secreted neurotrophins bind to and activate trk receptors in the pre- and post-synaptic membranes. Neurotrophin NT-3 also binds to trkB but with much less specificity than to trkC. Binding of the neurotrophins to the trk receptors leads to receptor tyrosine phosphorylation. The phosphorylation process triggers the activation of molecular cascades or pathways that control cell functioning. At the same time, binding of the neurotrophins to receptor p75 is non-specific. By itself, the receptor is unable to mediate any of neurotrophin actions but its presence is required for certain cell functions, most notably apoptosis.

Neurotrophic factors are a key element in establishment and maintenance of synapses. Neurotrophins secreted by the postsynaptic cell are likely to be highly localised owing to their propensity to bind to the cell surface near the secretion site. Endogenous neurotrophins, secreted in response to synaptic activity, induce the morphological changes that lead to the maintenance of the existing synapses or formation of new synaptic contacts. In the absence of signals, synaptic contacts may disconnect, breaking the particular neural pathway. Synaptic action of neurotrophins consists of two modes. In a resting "permissive" mode, neurotrophins are secreted at a low level through constitutive secretion or regulated secretion triggered by subthreshold and low-frequency synaptic activity. This permissive mode provides trophic regulation of synaptic functions, including the ability to generate long-term potentiation. In the active "instructive" mode, neurotrophic factors are secreted as a higher level of response to intense synaptic activity that results in a transient high-level calcium concentration in the post-synaptic cytoplasm. The secretion of neurotrophins may be supplemented by activity-dependent synthesis and transport of neurotrophins. The high level of neurotrophins then induce the modification of synaptic functions and the formation of new synaptic contacts.

In a further embodiment, the neurotrophic factors that are released from the neurons by delivery of the plasticity informative stimuli are neurotrophic factors that increase the survival of spiral ganglion cells. Such cells must function if an implantee is to successfully use a cochlear implant.

In another embodiment, the neurotrophic factors that are released from the neurons by delivery of the stimuli are neurotrophic factors that may decrease the neuron firing threshold. A decrease in threshold may reduce the power consumption of the apparatus or a stimulating device used in conjunction with the apparatus, such as a cochlear implant device.

In a still further embodiment, the stimuli is used to elicit outgrow of spiral ganglion cells towards stimulating electrodes used by the cochlear implant that is delivering the stimulus. By decreasing the distance between these cells and the stimulating electrode, a better selectivity and sensitivity of the auditory informative stimuli may be achieved.

The plasticity informative stimuli delivered to the cochlea is adapted to elicit production and/or release of naturally occurring agents and exercise such control to condition the first four out of five levels of the neural organisation, that is:

1. Individual cells, e.g. spiral ganglion cells;
2. Pairs of cells connected by synapses, e.g. cochlear nucleus;
3. Networks of interacting cells, e.g. nucleus of the lateral leminiscus or inferior colliculus; and
4. Systems in the brain that regulate behaviour, e.g. the auditory cortex.

As a consequence, the fifth level of neural organization, behavior of a recipient, may also be controlled as the recipient may act in response to the auditory informative stimuli in a different manner to that of a recipient of the very same auditory informative stimuli who has not received plasticity informative stimuli.

The plasticity informative stimuli is adapted to elicit production and/or release of naturally occurring agents and can be delivered to the auditory system at the first four out of five levels of the neural organisation, that is:

1. Individual cells, eg. spiral ganglion cells (by eg. CI, endosteal electrode);
2. Pairs of cells connected by synapses, e.g. cochlear nucleus (by e.g. ABI);
3. Networks of interacting cells, e.g. nucleus of the lateral leminiscus or inferior colliculus (e.g. MBI); and
4. Systems in the brain that regulate behaviour, e.g. the auditory cortex (e.g. a visual cortical implant).

The stimuli exercise such control to condition the level of the neural organisation at which is applied and levels above the level at which the said stimuli is applied.

The plasticity informative stimuli is preferably delivered to the cochlea at a frequency less than 5 kHz, more preferably less than 2 kHz, and still more preferably much lower than this frequency. In one embodiment, the frequency can be between 1 and 100 Hz. In another embodiment the frequency can be between 10 and 100 Hz. In another embodiment, the frequency can be between 20 and 100 Hz. In another embodiment the frequency can be about 50 Hz.

In a further embodiment, the delivery of plasticity informative stimuli can occur at times when the apparatus is incapable of or is not delivering auditory informative stimuli. For example, the delivery of plasticity informative stimuli can occur when the implantee is asleep and not using the apparatus for the delivery of auditory informative stimuli.

The apparatus can be adapted to deliver stimuli when the implantee is asleep. The controller can include a clock device that controls this function. For example, the stimuli can be delivered for a predetermined period of time. The controller can also monitor and measure the time that has elapsed since the last auditory informative stimulus was delivered by the apparatus, if the apparatus is adapted to do so.

As described above, the apparatus can comprise a cochlear implant. As described, a cochlear implant bypasses the hair cells in the cochlea and directly delivers electrical stimulation to the auditory nerve fibres, thereby allowing the brain to perceive a hearing sensation resembling the natural hearing sensation normally delivered to the auditory nerve. U.S. Pat. No. 4,532,930, the contents of which are incorporated herein by reference, provides a description of one type of cochlear implant system that could be modified to deliver the plasticity informative stimuli.

In one embodiment, the cochlear implant system preferably comprises two main components, namely an external component commonly referred to as a processor unit, and an implantable internal component commonly referred to as a stimulator/receiver unit. These components preferably cooperate together to provide the sound sensation to an implantee.

The external component can comprise a microphone for detecting sounds, such as speech and environmental sounds, a speech processor that converts speech detected by the microphone into a coded signal, a power source such as a rechargeable or non-rechargeable battery, and an external antenna transmitter coil.

The coded signal output by the speech processor is preferably transmitted transcutaneously to the implanted stimulator/receiver unit situated within a recess of the temporal bone of the implantee. This transcutaneous transmission occurs through use of an inductive coupling provided between the external antenna coil which is positioned to communicate with an implanted antenna receiver coil provided with the stimulator/receiver unit.

This communication serves two essential purposes, firstly to transcutaneously transmit the coded sound signal and secondly to provide power to the implanted stimulator/receiver unit. This link is preferably in the form of a frequency modulated (FM) radio frequency (RF) link.

The implanted stimulator/receiver unit preferably comprises the antenna receiver coil that receives the coded signal and power from the external processor component, and a stimulator that processes the coded signal and outputs a stimulation signal to an intracochlea electrode assembly which applies the electrical stimulation directly to the auditory nerve. In normal operation, the electrical stimulation is preferably such to produce a hearing sensation in the implantee that corresponds to the sound originally detected by the microphone of the external component.

The external componentry of the cochlear implant can be carried on the body of the implantee, such as in a pocket of the implantee's clothing, a belt pouch or in a harness, while the microphone can be mounted on a clip mounted behind the ear or on a clothing lapel of the implantee.

In another embodiment, the external componentry can be housed in a small unit capable of being worn behind the ear of the implantee.

In another embodiment, the cochlear implant can be capable of being totally implantable within the implantee. In one example of such a system, the totally implantable cochlear system can have the features of the system described in International Application No PCT/AU01/00769, the contents of which is incorporated herein by reference.

In one embodiment, the system can have an implantable unit comprising:
(i) a hermetically sealed housing including:
(a) a power source that provides the power requirements of the implantable unit.
In another embodiment, the housing can further house:
(b) a microphone that detects sounds and outputs acoustic signals representative of said detected sounds; and
(c) a processor device that receives said acoustic signals from the microphone and converts the signals into stimulation signals representative of the detected sounds.

In a preferred embodiment, the hermetically sealed housing is, when used, implanted in a recess formed in the temporal bone adjacent the ear of the implantee that is to receive the implant in a conventional manner as perfected through the implantation of conventional implants.

In a preferred embodiment, the housing is formed from a biocompatible material. Preferably, the housing is manufactured from titanium and is hermetically sealed before implantation into an implantee.

In a preferred embodiment, the unit is formed so as to minimise the need for bone excavation from the temporal bone. The unit preferably has similar dimensions to a conventional implant therefore allowing similar surgical procedures to be employed during implantation.

The housing is preferably made with a smooth surface or surfaces. The housing is also preferably coated with an additional protective layer, such as a layer of silicone or parylene.

In this embodiment, the microphone is preferably housed within the housing. The microphone can be mounted at or adjacent an outer surface of the housing.

The microphone can be a directional dual cavity microphone or a single cavity microphone. A dual-cavity microphone provides an effective means of rejecting common mode body-conducted noise emanating from body functions, such as chewing, respiration and blood flow.

It is also envisaged that the microphone can be an electret-type microphone. In another embodiment, the microphone can utilise a piezoelectric polymer, such as polyvinylidene fluoride (PVDF), or a piezoceramic material.

The microphone can comprise a hearing aid microphone as known in the art. An example of a suitable microphone is a Knowles microphone.

Preferably, the microphone of the totally implantable system will function at a pressure ranging from 1.5 atm 0.7 atm. This allows a wearer to still use the implant system while recreational diving or during flights on commercial or light aircraft or at elevated locations. The microphone will preferably still operate after being subject to a pressure outside the above range. Preferably, the microphone will survive any exposure to a pressure in the 5 atm to 0.5 atm range.

The implant system, whether totally implantable or not, will further comprise an electrode array suitable for insertion in the cochlea of an implantee. The array once inserted is adapted to receive stimulation signals and, in part, output auditory informative stimuli to the implantee's auditory nerve. The array is also preferably adapted to output the plasticity informative stimuli as described herein.

The electrode array can comprise an elongate electrode carrier member having a plurality of electrodes mounted thereon. The carrier member is preferably formed from a suitable biocompatible material. In one embodiment, the material can be a silicone, such as Silastic MDX 4-4210. In another embodiment, the elongate member can be formed from a polyurethane.

Each electrode is also preferably formed from a biocompatible material, such as platinum. In one embodiment, the electrode array can comprise 22 platinum electrodes spaced along the carrier member.

The carrier member can preferably be capable of adopting or being moved into a first configuration to allow said member to be inserted into an implantee's cochlea. Still further, the carrier member is preferably capable of adopting or being moved into at least a second configuration wherein said elongate member is curved to match a surface of said cochlea.

A stiffening element, such as a metallic stylet or bioresorbable stiffening element can be used to bias the elongate member into said first configuration. On implantation, the stylet can be withdrawn or the stiffening element can dissolve, or at least soften, to allow the carrier member to adopt its preferred second configuration.

In a preferred embodiment, the first configuration is preferably substantially straight. More preferably, the first configuration is straight. The second configuration is preferably curved, more preferably spirally curved.

In a further embodiment, the elongate member can have a resiliently flexible tip member extending forwardly from the first end of the body. The tip member can serve to help minimise the trauma caused to the cochlea on insertion of the array.

Where utilised, the bioresorbable material of the stiffening element can be selected from the group consisting of polyacrylic acid (PAA), polyvinyl alcohol (PVA), polylactic acid (PLA) and polyglycolic acid (PGA). Other materials could also be used which provide the characteristics required for the particular application.

In a further embodiment, at least a portion of an outer surface of the elongate member can have a coating of a lubricious material. In one embodiment, a substantial portion or the entire outer surface of the elongate member can have a coating of the lubricious material.

In this embodiment, the lubricious material can be selected from the group comprising polyacrylic acid (PAA), polyvinyl alcohol (PVA), polylactic acid (PLA) and polyglycolic acid (PGA). It is envisaged that other similar materials could also be used.

The implant system can also include one or more capacitively coupled extracochlea electrodes to support monopolar stimulation as is known in the art.

In one embodiment, the at least one electrode member of the apparatus can be adapted to deliver both the plasticity informative stimuli and the auditory informative stimuli to the cochlea.

In another embodiment, the apparatus can comprises at least one electrode member and a further said at least one electrode member. In this case, the further at least one electrode member is preferably adapted to deliver auditory informative stimuli while the electrode member is adapted to deliver plasticity informative stimuli.

The at least one electrode member is preferably part of an electrode array suitable for insertion in the cochlea of an implantee. In a further embodiment, the at least one electrode member is part of a first electrode array and the further at least one electrode member is part of a second electrode array.

The electrodes of the electrode array or the first and second electrode arrays can receive stimulation signals from an implanted stimulator device of the implantable component. The stimulator device is preferably electrically connected to the elongate member of the electrode array by way of an electrical lead. The lead can include the one or more wires extending from each electrode of the array mounted on the elongate member. A single lead can extend from the stimulator device to the first and second electrode arrays. In another embodiment, separate leads can extend from the stimulator device to the respective electrode arrays. In a still further embodiment, the apparatus can have a first stimulator device for providing stimulation signals to the first electrode array for delivering plasticity informative stimuli to the cochlea and a second stimulator device for providing stimulation signals to the second electrode array for delivering auditory informative stimuli to the cochlea.

In one embodiment, the lead can extend from the elongate member to the stimulator device or at least the housing thereof. In one embodiment, the lead is continuous with no electrical connectors, at least external the housing of the stimulator device, required to connect the wires extending from the electrodes to the stimulator device. One advantage of this arrangement is that there is no requirement for the surgeon implanting the device to make the necessary electrical connection between the wires extending from the electrodes and the stimulator device. Electrical connection between the processor device within the housing and the electrode array and the one or more extracochlea electrodes can also be provided by respective hermetic and insulated ceramic feedthroughs. Each feedthrough can be formed using the method described in U.S. Pat. No. 5,046,242, the contents of which are incorporated herein by reference.

It is also envisaged that the present invention does not necessarily require that the stimulating electrodes be positioned on an elongated electrode carrier member. It is possible for the stimulating electrodes and stimulator housing (housing the electronics, power source, RF antenna) to be fabricated as an integral device. In this regard, the electronics are positioned in close proximity to the stimulating electrodes with only a relatively thin impermeable barrier separating the electrodes from the electronics components.

As described, the housing of the implantable unit houses a power source, such as one or more rechargeable batteries. This power source can have sufficient power to allow the implant to deliver plasticity informative stimuli even when the external component is not being used and the implantee is unable to receive auditory informative stimuli. This is advantageous as it allows the system to deliver the plasticity informative stimuli such as when the implantee is asleep.

In this regard, the electronics housed in the implantable unit is provided with a clock, controlling the overall operation of the device. This clock can control the timing with which the predetermined stimulation pattern can occur. This clock can be programmable to operate in "real time" such that the recipient can receive plasticity informative stimuli at times when the recipient is asleep or not receiving auditory informative stimuli. Such a clock would ideally take into consideration time changes and personal settings, such as shift work etc, and would therefore be controllable through an external device, such as a conventional external speech processor.

In a further aspect, the present invention is an implantable apparatus for delivering electrical plasticity informative stimuli and auditory informative stimuli to the auditory system of an implantee, comprising:
 (i) a power source that provides power for the apparatus;
 (ii) a stimulator device that outputs stimulation signals; and
 (iii) at least one electrode member that receives the stimulation signals and delivers said stimuli to the auditory system of the implantee in response to said signals;
 wherein the stimuli facilitates and/or controls the production and/or release of naturally occurring agents into the auditory system of the implantee to influence the neural plasticity thereof.

In a preferred embodiment, the stimuli modifies the functionality of the auditory system in a predetermined desired manner. In particular, the present invention preferably provides an apparatus that can make controlled rearrangement of the neural network.

In a preferred embodiment, the apparatus is adapted to deliver stimuli to the auditory system of the implantee. The stimuli can be delivered to the cochlea (e.g. via intracochlear electrode or endosteal electrode), the cochlear nucleus (e.g. via an ABI electrode), the inferior colliculus (e.g. via a MBI electrode), or any other part of the auditory system.

Further, the stimulus can be delivered to the Subthalamic Nucleus (STN), the Globus Pallidus (GPi), and/or the Thalamus of the implantee requiring deep brain stimulation techniques.

In this and other aspects, the stimulator device can be adapted to monitor or detect when the at least one electrode member is not delivering auditory informative stimuli. On monitoring or detecting that no auditory informative stimuli is being delivered by the electrode member, the apparatus can commence delivery of plasticity informative stimuli.

In a further embodiment of this and other aspects, the apparatus can detect when transcutaneous signals from an external controller have stopped, such as due to deactivation of the external controller or removal from the implantee, and so commence delivery of plasticity informative stimuli. In this regard, the stimulator device can be adapted to delay delivery of plasticity informative stimuli until a predetermined time period since delivery of the last auditory informative stimuli. The time period can be, for example, in the range of a few seconds to hours as prescribed by a clinician or other person responsible for the maintenance and functioning of the apparatus. Such persons may include medical practitioners, audiologists, and hearing prosthesis engineers.

The delivery of the plasticity informative stimuli is preferably programmed into the apparatus, such as the stimulator device or the controller. The programming can be predetermined and comprise a predetermined pattern and type of delivery of stimuli. The stimuli can be adapted to be delivered during a regularly occurring activity such as sleep and/or sport activities when the implant is typically not in use, such as swimming. The stimuli can be adapted to be delivered in unusual or unexpected circumstances, such as when there is a failure of the implantee's speech processor, if they have one, or the occurrence of an injury that prevents the implantee wearing their speech processor, e.g. an injury to the head, ear, skin.

The type of stimuli can also have a predetermined paradigm and/or stimulating pattern. The type of stimuli can also depend on feedback received by the apparatus. For example, the type of stimuli can depend on whether auditory informative stimuli has been delivered and the time that has elapsed since the last delivery of auditory informative stimuli. It can also be dependent on the overall stimulation level provided over a predetermined period of time, such as over one day.

The stimuli can also vary depending on the nature of the neural network that is receiving the stimuli.

The stimulator device can continue to deliver plasticity informative stimuli until such time as the system recommences delivery of auditory informative stimuli or the on-board battery is discharged. When being used, the external controller can be used to recharge an on-board battery using the transcutaneous inductive coupling.

In this aspect, the at least one electrode can be part of an electrode array that comprises an elongate electrode carrier member having the plurality of electrodes thereon.

In a still further embodiment, the carrier member on at least implantation into the auditory system can have a delivery mechanism that delivers appropriate agents, preferably naturally occurring agents or agents controlling and/or facilitating the production and/or release of naturally occurring agents. In one embodiment, the agents can be neurotrophic factors.

The agent delivered to the auditory system can be:
 (1) the desired agent which acts on the auditory system, or
 (2) a precursor for the desired agent that acts on the auditory system The precursor for the desired agent can be in a form similar to that of the desired agent which undergoes a chemical, physical or biological change to take the form of the desired agent or can be an agent, action of which causes formation of the desired agent (e.g. gene injection where gene itself is not the desired agent but activation of the gene produces the desired agent; e.g. a BNDF gene is not a desired agent but its action controls production and secretion of BDNF).

The delivery mechanism may be in the form of a coating, comprising a slow-releasing film containing neurotrophic factors. It is considered that such an initial dose of neurotrophic or other factors may be required to initiate the cell response which will be then maintained by electrical stimulation. In addition or instead, the carrier member can be used to deliver neurotrophic factors to the site of implantation of the carrier member. In this regard, the implant can further comprise a fluid reservoir and pumping device that is adapted to pump neurotrophic factors out of the carrier member and into the auditory system.

Further, the agent can be added in an acute manner during the surgical procedure, where the device does not feature any additional component to those previously described. The agent is, for example, added by injection during surgery.

More then one agent can be delivered to the auditory system. The agents can be delivered simultaneously, or sequentially, in predetermined manner.

If more than one agent is administered, the administration of all drugs can be:
1. uniform along the target organ, or
2. place and/or time specific, where at least one drug is preferably administered to one part of the target organ, e.g. the apical part of the cochlea and another drug is preferably administered to another part of the target organ, e.g. the basal part of the cochlea.

Administration of the drugs can occur simultaneously or at different times.

While the above description has concentrated on describing use of a modified cochlear implant to deliver the plasticity informative stimuli, such stimuli could be delivered using a device that is implanted in conjunction with or instead of a cochlear implant. Still further, the apparatus could be installed to deliver plasticity informative stimuli to the cochlea of the patient that is not receiving the cochlear implant. For example, delivery of plasticity informative stimuli may be performed in conjunction with use of a middle ear implant or a hearing aid.

In one embodiment, the plasticity informative stimuli is preferably delivered in a duty cycle comprising a period of time ($t1$) of active stimulus and a period of time ($t2$) of no stimulus. The period of time ($t1$) preferably comprises a relatively short period of time of relatively high frequency stimulus (active part) followed by a relatively long period of time ($t2$) of no activity (inactive part), ie. $t1<t2$, where $t1:t2$ is at least about 0.2 or smaller. In this embodiment, $t1$ can be in the range of about 0.001 seconds to about 100 seconds.

As mentioned, the total period of time between two stimulations ($t1+t2$) is defined as a duty cycle. In this embodiment, the duty cycle is the basic unit of a plasticity informative stimulus. The nature and repetition rate of the duty cycle can preferably be prescribed by the clinician responsible for the implantee's apparatus. In one embodiment, the duty cycles can be repeated, for each individual channel, in a sequence $t_1$-$t_2$, $t_1$-$t_2$, $t_1$-$t_2$, $t_1$-$t_2$ and so on. In another embodiment, a pause can be provided between duty cycles. The length of the pause can be variable. For example only, a number of duty cycles can be applied in a sequence as shown previously ($t_1$-$t_2$, $t_1$-$t_2$, $t_1$-$t_2$, $t_1$-$t_2$). Then, each of group of such a plurality of cycles can be separated by a pause (a period of non-activity) $t_3$. For example:

($t_1$-$t_2$, $t_1$-$t_2$, $t_1$-$t_2$, $t_1$-$t_2$)-$t_3$-($t_1$-$t_2$, $t_1$-$t_2$, $t_1$-$t_2$, $t_1$-$t_2$)-$t_3$-($t_1$-$t_2$, $t_1$-$t_2$, $t_1$-$t_2$,$t_1$-$t_2$)-$t_3$-($t_1$-$t_2$, $t_1$-$t_2$, $t_1$-$t_2$, $t_1$-$t_2$)

In this case, $t_3$ is preferably significantly longer than either of $t_1$ or $t_2$. It will be appreciated that any combination of the duty cycles and pauses between them could be utilised by the present invention as thought appropriate by the consulting clinician.

As defined above, the carrier member can have a plurality of electrodes, otherwise known as stimulating pads. On implantation, each electrode has a slightly different position with regard to the tissue that is being stimulated. Still further, the plasticity informative stimuli may be applied to a single stimulating channel, some stimulating channels or all stimulating channels of the array. Further, plasticity informative stimuli, when applied to multiple stimulating electrodes, can be applied either simultaneously or sequentially with regard to the active part of the duty cycle.

It is envisaged that the plasticity informative stimuli may feature one and only duty cycle (DC). Alternatively, the plasticity informative stimuli can feature more then one duty cycle. Any combination of two or more duty cycles is possible, eg.:

DC1-DC1-DC1-DC1-LP-DC2-DC2-DC2-DC2 where LP=long pause that is longer than DC1 or DC2; or

DC1-DC2-DC1-DC2

All electrodes deliver the same stimulation pattern, eg. DC1-DC1-LP-DC2-DC2

Each electrode can deliver various stimulation patterns but all electrodes deliver the same pattern at the time.

Each electrode can deliver various stimulation patterns and each electrode deliver pattern which may be different from other electrodes. In other words, the delivery of plasticity informative stimuli as defined by duty cycle, is place specific. For example, one pattern of stimulation may be applicable to the basal turn of the cochlea and another pattern of stimulation may be applicable to the apical part of the cochlea.

Delivery of plasticity informative stimuli can be coincident with delivery of drug(s) for at least a period of time. Delivery of the stimuli and drug can be place and time specific, e.g. one type of drug and/or stimuli is applied to the basal part of the cochlea and another type of the drug and/or stimuli is applied to the apical part of the cochlea.

For simplicity in all cases the cochlea is divided into the basal part and apical part but the plasticity informative stimuli and/or agents can be delivered in a much larger number of sectors. Effectively, as far as plasticity informative stimuli is concerned, a total number of stimulating pads+a total number of virtual channels determines the maximum number of independent sectors that the plasticity informative stimuli can be delivered to.

For example, in a simultaneous mode, multiple, if not all, of the electrodes can be activated simultaneously, with the active part of the duty cycle being applied to all or some active channels, ie. the active part of the duty cycle for each active electrode occurs simultaneously.

In another embodiment, if the stimuli are applied to multiple, if not all, stimulating electrodes, in a sequential mode, the active part of the duty cycle for one stimulating electrode occurs when all other electrodes are in the inactive part of the duty cycle, so at any given time only one stimulating electrode is active.

Still further, the stimuli can be applied to multiple if not all, stimulating electrodes, in a semi-sequential mode, where the beginning of the active part of the duty cycle for some or all stimulating electrodes is shifted in time so that the stimulation from one electrode occurs with a delay with the respect to other stimulating electrodes, but before the active part of the duty cycle is finished.

Still further, the plasticity informative stimulation pattern can be a combination of all of the above mentioned modes.

In another example, plasticity informative stimuli can be applied sequentially in which multiple duty cycles are delivered through one stimulating electrode before it is applied on another stimulating electrode of the array.

The plasticity informative stimuli modes, such as those described above, can be delivered according to a predetermined sequence, or be dependent on the activity of the stimulating electrodes carrying the auditory informative stimuli.

In another example, the apparatus measures the activity of one or more of the stimulating electrodes delivering auditory informative stimuli over a period of use, such as a day. For example, the apparatus can measure the frequency of stimulation, the stimulation current, and/or the neural response for each of stimulating electrodes. In this case, the apparatus can, for example, measure the different level of activity during the day exhibited by each of the electrodes and so provide a measure of the activity and/or the differences therebetween of the auditory fibres located along the cochlea.

In this case, the plasticity informative stimuli delivered by each electrode can be varied depending on the measure of activity determined for that electrode over the preceding time period. The delivery of the plasticity informative stimuli can be varied such that the overall stimulation received by the auditory fibres from any particular electrode over a predetermined period of time is substantially equal or the same as other auditory fibres receiving stimulation from other electrodes in the array.

In such circumstances, an algorithm may be used to control electrical stimulation carrying plasticity informative stimuli. For any stimulating electrode, $N_0$ delivering auditory informative stimuli, a corresponding weighting function $W_0$ could be calculated according to:

$$W_0 = \Sigma(T_i \times E_i \times N_i), i \text{ being between 1 and } n$$

where
n is a total number of stimulating electrodes;
$N_0$ is the stimulating electrode for which weight is being calculated;
$T_i$ is time of stimulus;
$E_i$ is amplitude of stimulus; and
$N_i$ is contribution factor for the particular electrode; $N_0$ has the strongest contribution and electrodes positioned further from $N_0$ have decreasing contribution but not necessarily in a uniformly decreasing manner.

In a similar manner, a weighting function Wp for the plasticity informative stimuli can be calculated:

$$Wp_0 = \Sigma(Tpi \times Epi \times Npi), i \text{ being between 1 and } n$$

where
n is a total number of stimulating electrodes;
$N_0$ is the stimulating electrode for which weight is being calculated;
$Tp_i$ is time of stimulus;
$Ep_i$ is amplitude of stimulus; and
$Np_i$ is contribution factor for the particular electrode; $N_0$ has the strongest contribution and electrodes positioned further from $N_0$ have decreasing contribution but not necessarily in a uniformly decreasing manner.

In this way, the effect of direct stimulation is taken into account as well as the stimulation delivered by adjoining stimulating electrodes. The "auditory" probability (Pa) for each particular stimulating electrode to deliver plasticity informative stimuli is then a function of the weight (Wi) of auditory informative stimuli, $Pa_i = f(Wi)$. The function that relates the weight of auditory informative stimuli and probability of delivering plasticity informative stimulus is complex. Further, the "plasticity" probability (Pp) for each particular stimulating electrode to deliver plasticity informative stimuli is then a function of the weight (Wpi) of plasticity informative stimuli, $Pp_i = f(Wpi)$.

The total probability for each particular stimulating electrode to deliver plasticity informative stimuli is then a function of the weight of the auditory and plasticity informative stimuli:

$$P = f(Pa, Pp)$$

In another embodiment, both auditory and plasticity informative stimuli may be delivered together.

In yet another embodiment, the auditory informative stimuli is superimposed on the plasticity informative stimuli.

In a still further embodiment, the system monitors the activity of the electrodes and determines the weight of the auditory informative stimuli, similar to the above formula. The probability of the stimulating electrode delivering plasticity informative stimuli can be inversely proportional to the auditory informative stimuli weight $W_x$. The result is that the longer the period of time a neuron spends without being active (firing), the higher the probability that that stimulating electrode will deliver plasticity informative stimuli to the auditory system, $P_{xi} = f(1N/W_i)$, $W_{xi} = f(t_{xi})$, where $P_{xi}$ is the probability of delivering plasticity informative stimuli, related to a period of auditory informative stimulus inactivity, $W_{xi}$ is the weight of auditory informative stimuli and is proportional to the period of time without auditory informative stimuli $t_{xi}$.

The stimulation strategy that delivers plasticity informative stimuli can depend on individual circumstances, such as the speech coding strategy used by an implantee's cochlear implant. By applying plasticity informative stimuli, the entire auditory system may be stimulated, so maintaining its plasticity.

The apparatus can have more than one input. One input is a programming system which can be used to set desired parameters of the apparatus. Another input can rely on using functions such as described above (Wi, Wp, Wa, P, Pa, Pp) and then provide the result to the apparatus. The system may receive input from the apparatus as well as an adjoining stimulating device, if present, e.g. cochlear implant or other auditory informative stimulus. It is important to note that the system can receive input from the stimulator part of the device, hence it measures electronic output of the stimulating electrodes.

In another case, a neural response telemetry (NRT) capability can be used to create a function which then measures the neural activity as a response to the stimulating signal. Hence this function may be provided as an input to apparatus.

Overall, the probability of plasticity informative stimuli, in a case it is not predetermined, may be represented as a function of:

$$P = f\{(c_{a(PIVTF)} \times P_{a(PIVTF)}), (c_{a(NRT\,PIVTF)} \times P_{a(NRT\,PIVTF)}), (c_{p(PIVTF)} \times P_{p(PIVTF)}), (c_{p(NRT\,PIVTF)} \times P_{p(NRT\,PIVTF)})\}$$

where:
c is a contributing coefficient for each of the probabilities;
Index a is related to auditory informative stimulus;
Index p is related to plasticity informative stimulus;
Index PIVTF is related to input received from a function hereinafter called "Plastic Informative Variable Tracking Function"; and Index NRT PIVTF is related to input received from a NRT-based Plastic Informative Variable Tracking Function.

The present system may be functional in two modes, ie. acute and chronic. In the acute mode, the plasticity informative stimuli may be delivered to the auditory system over a short period of time when compared to the length of time that the cochlear implant is active. In the chronic mode, the plasticity informative stimuli may be presented over the same or comparable period of time as the length of time that the cochlear implant is active.

The stimulator device preferably comprises a processor that processes a set of instructions stored on the processor in the form of software.

According to a still further aspect, the present invention is a method of delivering stimuli to a neural network of an implantee comprising the steps of:
(i) positioning at least one electrode member in a position suitable to deliver said stimuli to said implantee;
(ii) generating stimulation signals;
(iii) transmitting said signals to said at least one electrode member; and
(iv) delivering said stimuli in response to said signals;
wherein the stimuli facilitates and/or controls the production and/or release of naturally occurring agents into the neural network to influence the neural plasticity thereof.

In this aspect, the stimuli preferably modifies the functionality of the neural network in a predetermined desired manner. In particular, the present invention preferably provides an apparatus that can make controlled rearrangement of the neural network.

In this aspect, step (i) preferably comprises positioning said at least one electrode member such that it is positioned in an auditory system of an implantee, such as the cochlea. In this embodiment, the at least one electrode is also preferably adapted to deliver auditory informative stimuli to the cochlea of the implantee. In another embodiment of this aspect, auditory informative stimuli may be delivered by a hearing prosthesis other than a cochlear implant, such as a middle ear implant (MEI) or a hearing aid (HA).

In this aspect, the method of delivering plasticity informative stimuli to a neural network of an implantee is preferably performed using an apparatus or implant having one or more of the features as defined herein.

For the purpose of this description, only chemical neuron-neuron synapse processes are described. Those skilled in art will recognise that the present invention may be similarly applied for the purpose of influencing plasticity of the neuron-effector tissue synapse.

BRIEF DESCRIPTION OF THE DRAWINGS

By way of example only, a preferred embodiment of the invention is now described with reference to the accompanying drawings, in which.

PREFERRED MODE OF CARRYING OUT THE INVENTION

Figure 1:
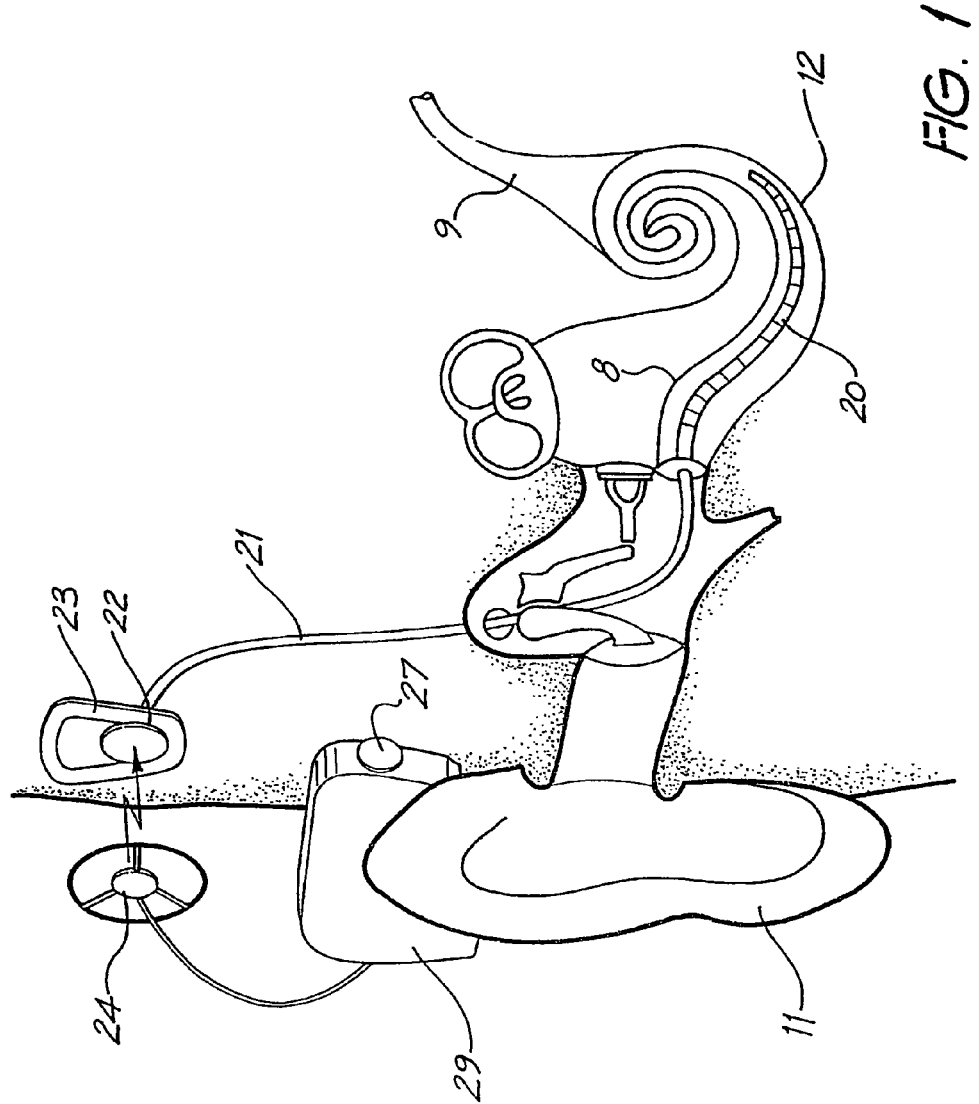
FIG. 1 is a pictorial representation of one example of a cochlear implant system according to the present invention.
Figure 9:
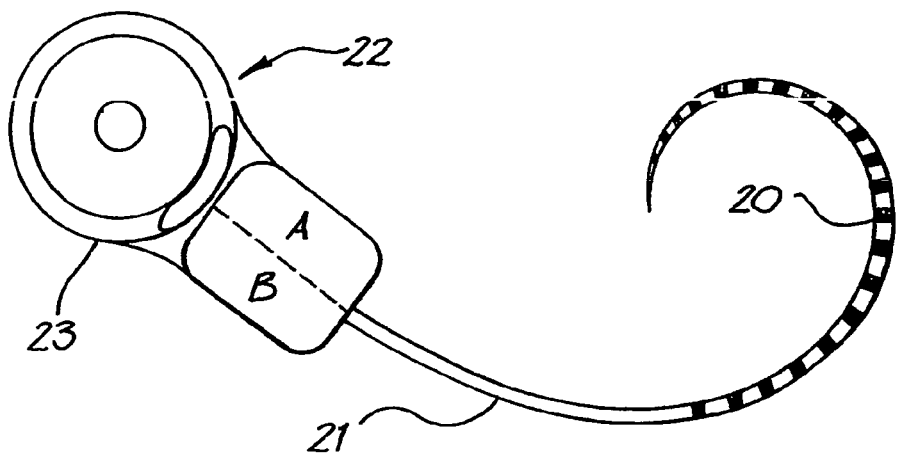
FIG. 9 is a simplified drawing of another embodiment of an apparatus according to the present invention.
Figure 10:
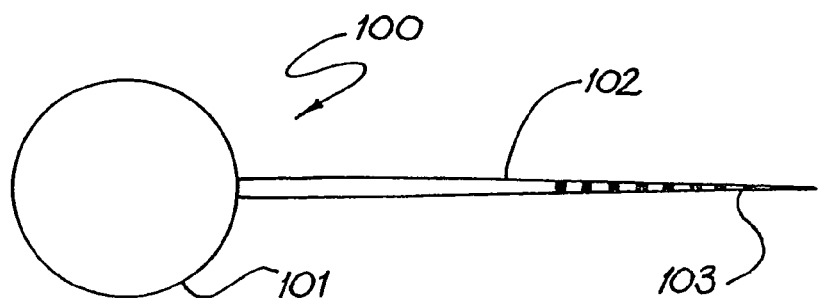
FIG. 10 is a simplified drawing of still further embodiment of an apparatus according to the present invention.

One embodiment of a cochlear implant for use in delivering plasticity informative stimuli in accordance with the present invention is depicted in FIGS. 1 and 9. While for the purposes of this description, a cochlear implant is depicted it will be appreciated that other devices for stimulating other locations of an implantee can be envisaged and are encompassed within the present application. For example, FIG. 10 depicts another embodiments of an implantable apparatus according to the present invention.

The cochlear implant of FIG. 1 comprises two main components, namely an external component including an external housing containing a speech processor 29, and an internal component including an implanted receiver and stimulator unit 22. The external component includes a microphone 27. The speech processor 29 is, in this illustration, constructed and arranged so that it can be mounted on and fit behind the outer ear 11. It will be understood that in an alternative version, the housing for the speech processor 29 and/or the microphone 27 may be worn on the body. Attached to the speech processor 29 is an external antenna coil 24 which transmits electrical signals to the implanted unit 22 via a frequency modulated (FM) radio frequency (RF) link.

The implanted component includes a receiver antenna coil 23 for receiving power and data from the transmitter coil 24. A cable 21 extends from the implanted receiver and stimulator unit 22 to the cochlea 12 and terminates in an electrode array 20. The signals thus received are applied by the array 20 to the basilar membrane 8 thereby stimulating the auditory nerve 9.

In addition to the array 20 being capable of delivering auditory stimuli to the basilar membrane 8, the cochlear implant is adapted to deliver plasticity informative stimuli to the basilar membrane 8. The delivery of such electrical stimulation has as its purpose the facilitation and control of the production and/or release of naturally occurring agents into the neural network of the implantee's auditory system to influence the neural plasticity thereof. As depicted in FIG. 9, the housing of the unit 22 can comprise a portion A that contains what would be regarded as the traditional circuitry of the implant so that the implant can function as a traditional cochlear implant. It also comprises a portion B that houses appropriate circuitry to allow the electrode array 20 to deliver plasticity informative stimuli as defined herein.

FIG. 10 depicts an alternative embodiment of the apparatus generally as 100 wherein the apparatus is simply adapted to deliver plasticity informative stimuli to a neural network, such as the auditory system. In this embodiment, the apparatus has a housing 101 for a stimulator device and an electrode array 102 extending therefrom. As depicted, the electrode array 102 can comprise a plurality of electrodes 103. The apparatus 100 depicted in FIG. 10 can be adapted to be implanted in the cochlea of an implantee. It could, however, also be implanted in other suitable locations. In the case of the auditory system, the array 102 could also be implanted within any of the cochlear nucleus (via an ABI device), the superior olive, the nucleus of the lateral lemniscus, the inferior colliculus (via a MBI device), the medial geniculate body, and the auditory cortex.

The plasticity informative stimuli has a magnitude less than the auditory perception threshold of the implantee and as such does not cause the implantee to perceive a sound in contrast to the case when the implant delivers an auditory stimuli.

Figure 11:
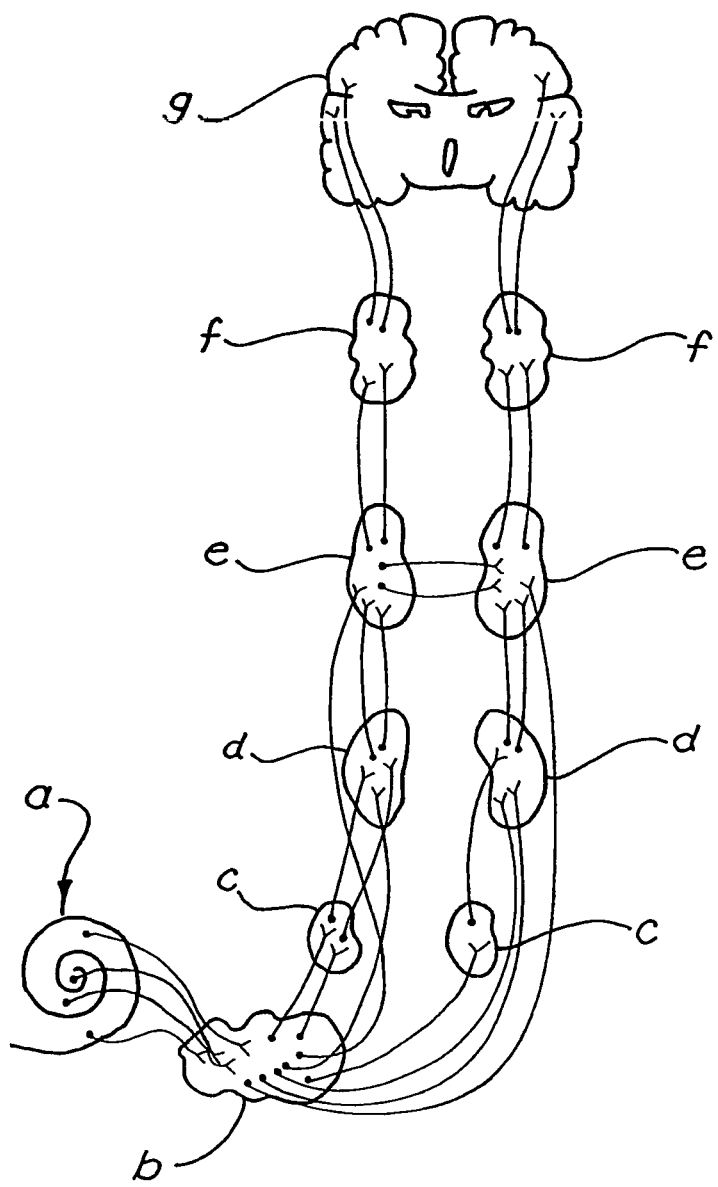
FIG. 11 is a schematic diagram of the human auditory system.

The plasticity informative stimuli when delivered to the cochlea 12 is transmitted through the central auditory system of the implantee, including the cochlear nuclei (CN), the superior olivary complex (SOC), the nuclei of the lateral lemniscus (NLL), the inferior colliculi (IC), the medial geniculate body (MGB) of the thalamus and the auditory cortex (AC). As described above, the CN, SOC, and NLL are brainstem nuclei, while the IC is at the midbrain level and the MGB and AC constitute the auditory thalamocortical system. A depiction of the auditory system is provided in FIG. 11 with:

(a) representing the cochlea.
(b) representing the cochlear nucleus
(c) representing the superior olive
(d) representing the nucleus of the lateral lemniscus
(e) representing the inferior colliculus
(f) representing the medial geniculate body
(g) representing the auditory cortex.

Delivery of such plasticity informative stimuli results in the production and release of said naturally occurring agents into the neural network to influence the neural plasticity thereof. The present devices have the advantage that the stimuli modifies the functionality of the neural network in a predetermined desired manner.

In the depicted embodiment, the naturally occurring agent that is produced and/or released is one or more neurotrophic factors or neurotrophins, such as Brain Derived Neurotrophic Factor (BDNF). In another embodiment, the neurotrophic factors can be selected from the group comprising NGF, NT-3, NT4/5, NT-6, LIF, GDNF, CNTF, and IGF-1.

In another embodiment, the said naturally occurring agents can comprise one of more factors, other then neurotrophins which have capacity to activate the neurotrophic receptors, for example adenosine, a neuromodulator.

Neurotrophic factors are a key element in establishment and maintenance of synapses. Neurotrophins secreted by the postsynaptic cell are likely to be highly localised owing to their propensity to bind to the cell surface near the secretion site. Endogenous neurotrophins, secreted in response to synaptic activity, induce the morphological changes that lead to the formation of new synaptic contacts. Synaptic action of neurotrophins consists of two modes. In a resting 'permissive' mode, neurotrophins are secreted at a low level through constitutive secretion or regulated secretion triggered by subthreshold and low-frequency synaptic activity. This permissive mode provides trophic regulation of synaptic functions, including the ability to generate long-term potentiation. In the active 'instructive' mode, neurotrophic factors are secreted as a higher level of response to intense synaptic activity that results in a transient high-level calcium concentration in the post-synaptic cytoplasm. The secretion of neurotrophins may be supplemented by activity-dependent synthesis and transport of neurotrophins. The high level of neurotrophins then induce the modification of synaptic functions and the formation of new synaptic contacts.

In a further embodiment, the neurotrophic factors that are released from the neurons by delivery of the plasticity informative stimuli are neurotrophic factors that increase the survival of spiral ganglion cells. Such cells must function if an implantee is to successfully use a cochlear implant.

Delivery of the plasticity informative stimuli can also be used to elicit outgrow of spiral ganglion cells towards the stimulating electrodes of the array 20. By decreasing the distance between these cells and the stimulating electrode, a better selectivity and sensitivity of the auditory informative stimuli may be achieved.

The plasticity informative stimuli delivered to the cochlea 12 is adapted to elicit production and/or release of naturally occurring agents and exercise such control to condition the first four out of five levels of the neural organisation, that is:

1. Individual cells, e.g. spiral ganglion cells;
2. Pairs of cells connected by synapses, e.g. cochlear nucleus;
3. Networks of interacting cells, e.g. nucleus of the lateral leminiscus or inferior colliculus; and
4. Systems in the brain that regulate behaviour, e.g. the auditory cortex.

As a consequence, the fifth level of neural organization, behavior of a recipient, may also be controlled as the recipient may act in response to the auditory informative stimuli in a different manner to that of a recipient of the very same auditory informative stimuli who has not received plasticity informative stimuli.

The plasticity informative stimuli is adapted to elicit production and/or release of naturally occurring agents and can be delivered to the auditory system at the first four out of five levels of the neural organisation, that is:

1. Individual cells, eg. spiral ganglion cells (by eg. CI, endosteal electrode);
2. Pairs of cells connected by synapses, e.g. cochlear nucleus (by e.g. ABI, PABI);
3. Networks of interacting cells, e.g. nucleus of the lateral leminiscus or inferior colliculus (e.g. MBI); and
4. Systems in the brain that regulate behaviour, e.g. the auditory cortex.

The stimuli exercise such control to condition the level of the neural organisation at which is applied and levels above the level at which the said stimuli is applied.

Figure 2:
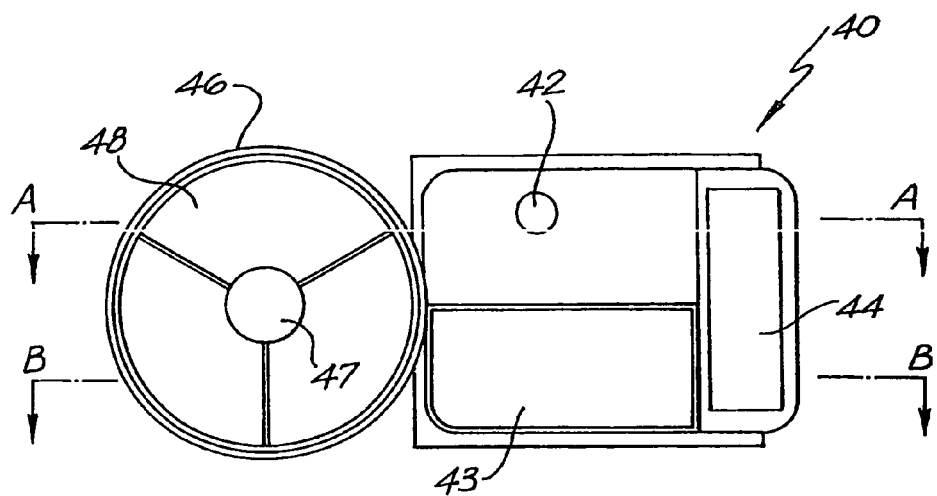
FIG. 2 is a plan view of an implantable housing for an implant according to one embodiment of the present invention.
Figure 2A:
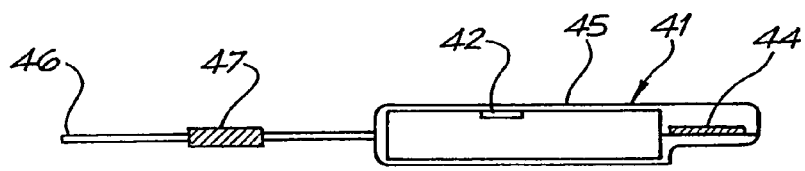
FIG. 2a is a cross-sectional view of the housing of FIG. 2 through line A-A of FIG. 2.
Figure 2B:
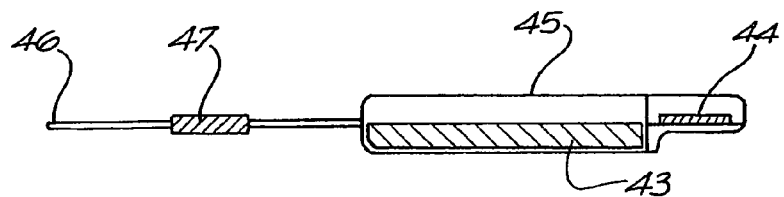
FIG. 2b is a further cross-sectional view of the housing of FIG. 2 through line B-B of FIG. 2.

FIGS. 2-2b depict another totally implantable cochlear implant system 40. The implant 40 is capable of operation, at least for a period of time, without reliance on componentry worn or carried external to the body of the implantee.

The implant 40 is adapted for implantation in a recess formed in the temporal bone adjacent the ear of the implantee that is receiving the implant. The implant 40 can be implanted in a manner similar to how the receiver and stimulator unit 22 depicted in FIG. 1 would be implanted.

The implant 40 comprises a biocompatible and hermetically sealed titanium housing 41 that houses the key electronic circuitry 44 of the implant 40. Also housed within the housing 41 are a microphone 42 and a rechargeable battery 43. Prior to implantation, the housing 41 is coated with a layer of silicone or parylene that serves to further protect the implant. Such a coating is well known in the art and will not be further discussed in this application.

As previously mentioned, the housing 41 is formed so as to minimise the need for bone excavation from the temporal bone at implantation.

In this particular embodiment, the microphone 42 is mounted such that its diaphragm is adjacent one of the surfaces 45 of the housing that faces outwardly following implantation of the housing 41. The depicted microphone 42 is a single cavity microphone but it is envisaged that other microphones, such as a directional dual cavity microphone, could be employed in this system which could perform an equal or similar function.

The electrode array used in conjunction with the implant 40 of the present invention is not shown but can be identical to the array 20 depicted in FIG. 1 or similar. It is, however, preferred that the implant 40 use a Contour™ array (Cochlear Limited, Lane Cove, NSW, Australia) in conjunction with corticosteroids to reduce the current required for stimulation.

The rechargeable battery 43 provides power for the microphone 42 and the electronic circuitry 44 housed within the housing 41. Numerous types of batteries could be used with a preferred choice being a lithium-ion battery. The type of battery chosen for this application depends greatly on the system requirements, as would be understood by those skilled in the art.

In the depicted embodiment, the battery 43 is non-removable from the housing 41. It will be appreciated that in other embodiments, the housing 41 could be modified to allow removal of the battery 43 by surgically accessing the housing 41.

The implant 40 is capable of operation whilst the battery 43 is being recharged. In order to isolate the battery from the entire package, a thermal and electrical insulating material is provided between the battery 43 and the surrounding housing 41.

The implant 40 includes an antenna coil 46, which is attached externally of the casing 41. The depicted coil 46 is a 3-turn electrically insulated platinum wire antenna coil. The electrical insulation for the depicted antenna coil 46 is provided by a flexible silicone moulding 48. The antenna coil 46 extends externally from the housing 41 as can be seen in FIG. 2.

The depicted antenna coil 46 is disposed about a centrally located rare earth permanent magnet 47 that is held in the centre of the antenna coil 46 by the silicone moulding 48 surrounding the antenna coil 46. The provision of the magnet 47 assists in the alignment of an external coil unit, such as the external coil 24 depicted in FIG. 1, with the implanted coil 46 via magnetic attractive forces, thereby providing for the system to be used as a conventional cochlear implant system. The magnet 47 is preferably surgically removable so as to allow the implantee to undergo, if required, magnetic resonance imaging (MRI) scanning.

Electrical connection between the coil 46 and the componentry within the housing 41 is provided by two hermetic and insulated ceramic feedthroughs. The coil 46 acts as part of a radio frequency (RF) link to allow bidirectional data transfer between the implant 40 and external devices. The coil 46 also acts a power receiver and so provides a means of inductively charging the battery 43 through the RF link.

The circuitry 44 within the housing is preferably mounted on a flexible circuit board to allow for easier provision of the circuitry within the housing 41. The circuitry 44 includes a speech processor and a stimulation processor incorporated within a single integrated circuit.

The stimulation processor within the circuitry 44 outputs auditory informative stimuli signals to an electrode array, such as array 20 of FIG. 1.

The array is also preferably adapted to output the plasticity informative stimuli as described herein.

The electrode array can comprise an elongate electrode carrier member having a plurality of electrodes mounted thereon. The carrier member is preferably formed from a suitable biocompatible material. In the embodiment depicted in FIG. 1, the material can be a silicone, such as Silastic MDX 4-4210.

Each electrode of the array 20 is also formed from a biocompatible material, such as platinum. In the depicted embodiment, the electrode array 20 comprises 22 platinum electrodes spaced along the carrier member.

The carrier member of the array 20 can have a first configuration to allow said member to be inserted into an implantee's cochlea 12 and at least a second configuration wherein the elongate member is curved to match a surface of said cochlea 12.

A stiffening element, such as a metallic stylet or bioresorbable stiffening element can be used to bias the elongate member into the first configuration. On implantation, the stylet can be withdrawn or the stiffening element can dissolve, or at least soften, to allow the carrier member to adopt its preferred second configuration. The first configuration is preferably substantially straight or straight, while the second configuration is curved or spirally curved.

Where utilised, the bioresorbable material of the stiffening element can be selected from the group consisting of polyacrylic acid (PAA), polyvinyl alcohol (PVA), polylactic acid (PLA) and polyglycolic acid (PGA). Other materials could also be used which provide the characteristics required for the particular application.

While not depicted, at least a portion of an outer surface of the elongate member can have a coating of a lubricious material. In one embodiment, a substantial portion or the entire outer surface of the elongate member can have a coating of the lubricious material. In this embodiment, the lubricious material can be selected from the group comprising polyacrylic acid (PAA), polyvinyl alcohol (PVA), polylactic acid (PLA) and polyglycolic acid (PGA). It is envisaged that other similar materials could also be used.

The implant system can also include one or more capacitively coupled extracochlea electrodes to support monopolar stimulation as is known in the art.

The electrodes of the array 20 can receive stimulation signals from the implanted stimulator processor making up part of the circuitry 44. The componentry within the housing 41 is electrically connected to the array 20 by way of an electrical lead, such as lead 21 depicted in FIG. 1. The lead 21 can include the one or more wires extending from each electrode of the array mounted on the elongate member.

As described, the housing 41 of the implantable unit houses a rechargeable battery 43. The battery 43 has sufficient power to allow the implant to deliver at least plasticity informative stimuli even when external componentry is not being used in conjunction with the implant 40 and the implantee is unable to receive auditory informative stimuli. This is advantageous as it allows the system to deliver the plasticity informative stimuli such as when the implantee is asleep.

In considering the embodiment depicted in FIGS. 2-2b, it should be appreciated that the implantable unit could be provide without a microphone 42 and speech processor. In this case, the detection of sound performed by the microphone and speech processing using a desired speech strategy could be performed using an external component such as processor 29 depicted in FIG. 1. In this case, the on-board battery 43 is used to power the circuitry 44 to ensure delivery only of plasticity informative stimuli to the array 20.

In this embodiment, the implant can be adapted to detect when the array 20 is not delivering auditory informative stimuli and so commence delivery of plasticity informative stimuli. The implant can detect when transcutaneous signals from an external controller, such as processor 29 have stopped, such as due to deactivation of the processor 29 or removal of the processor 29 from operation by the implantee, and so commence delivery of plasticity informative stimuli. In this regard, the stimulator device can be adapted to delay delivery of plasticity informative stimuli until a predetermined time period since delivery of the last auditory informative stimuli by the array 20. The time period can be, for example, in the range of a few seconds to hours.

The stimulator can continue to deliver plasticity informative stimuli until such time as the system recommences delivery of auditory informative stimuli or the on-board battery 43 is discharged. When being used, the external processor 29, having its own battery can be used to recharge the on-board battery 43 using the transcutaneous inductive coupling.

While not depicted, the carrier member of the array can be coated with a slow-releasing film containing neurotrophic factors. It is considered that such an initial dose of neurotrophic or other factors may be required to initiate the cell response which will be then maintained by electrical stimulation. In addition or instead, the carrier member can be used to deliver neurotrophic factors to the site of implantation of the carrier member. In this regard, the implant can comprise a fluid reservoir and pump (not depicted) that is adapted to pump neurotrophic factors out of the carrier member and into the cochlea.

While the above description has described use of a modified cochlear implant to deliver the plasticity informative stimuli, such stimuli could be delivered using a device that is implanted in conjunction with or instead of a cochlear implant. Still further, the apparatus could be installed to deliver plasticity informative stimuli to the cochlea 12 of the patient that is not receiving the cochlear implant.

The plasticity informative stimuli delivered by the depicted system to the cochlea 12 is at a frequency less than 5 kHz and preferably at or about 50 Hz.

Figure 3:
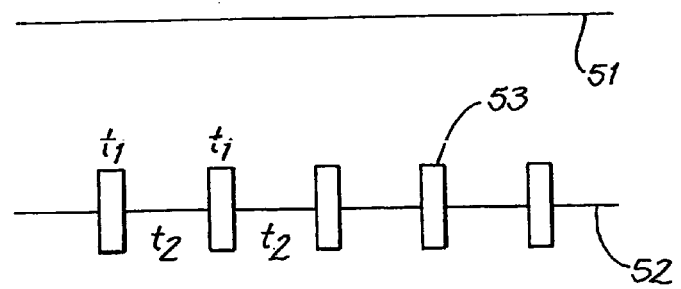
FIG. 3 is a depiction of plasticity informative stimuli as a function of time as output by the apparatus.

The delivery of plasticity informative stimuli also preferably occurs at times when the apparatus is incapable of delivering auditory informative stimuli. For example, the delivery of plasticity informative stimuli can occur when the implantee is asleep and not using the apparatus for the delivery of auditory informative stimuli. As depicted in FIG. 3, no auditory stimulation stimuli (line 51) is being delivered to the cochlea 12 and at this time, regular occurrences of plasticity informative stimuli 53 is being delivered to the cochlea 12.

Figure 4:
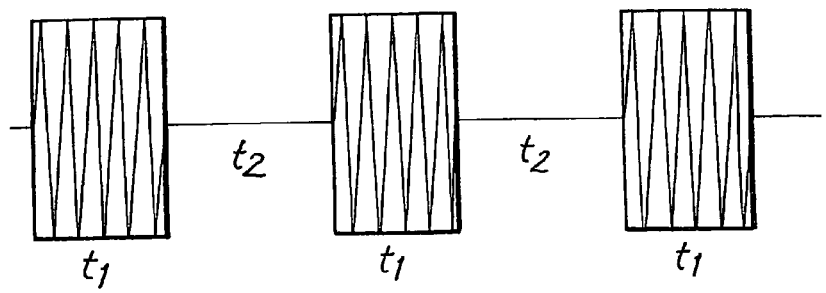
FIG. 4 is another depiction of plasticity informative stimuli as a function of time as output by the apparatus.

As depicted in FIG. 4, the pattern of the plasticity informative stimuli can comprise a short period (t1) of relatively high frequency stimulus 53 (active part) followed by a long period (t2) of no activity (inactive part), ie. t1<t2, where t1:t2 is at least about 0.2 or smaller. In this embodiment, t1 can be in the range of about 0.001 to about 100 sec. A total period between two stimulations 53 (t1+t2) is defined as a duty cycle. In this embodiment, the duty cycle is the basic unit of a plasticity informative stimulus.

As defined above, the array 20 can have a plurality of electrodes, otherwise known as stimulating pads. On implantation, each electrode has a slightly different position with regard to the tissue of the cochlea 12 that is being stimulated. Still further, the plasticity informative stimuli may be applied to a single stimulating channel, some stimulating channels or all stimulating channels of the array. Further, plasticity informative stimuli, when applied to multiple stimulating electrodes, can be applied either simultaneously or sequentially with regard to the active part of the duty cycle.

Figure 5:
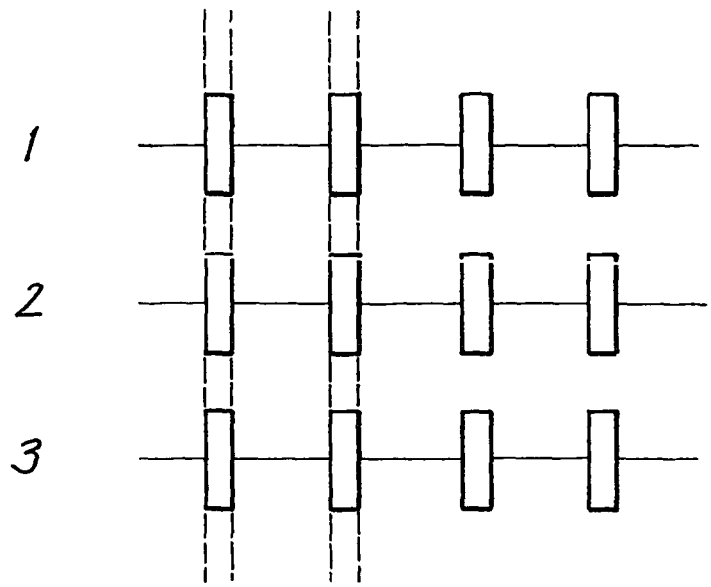
FIG. 5 is another depiction of plasticity informative stimuli as a function of time as output by the apparatus.

For example, in a simultaneous mode, multiple, if not all of the electrodes can be activated simultaneously, with the active part of the duty cycle being applied to all or some active channels, ie. the active part of the duty cycle for each active electrode occurs simultaneously (as depicted in FIG. 5).

Figure 6:
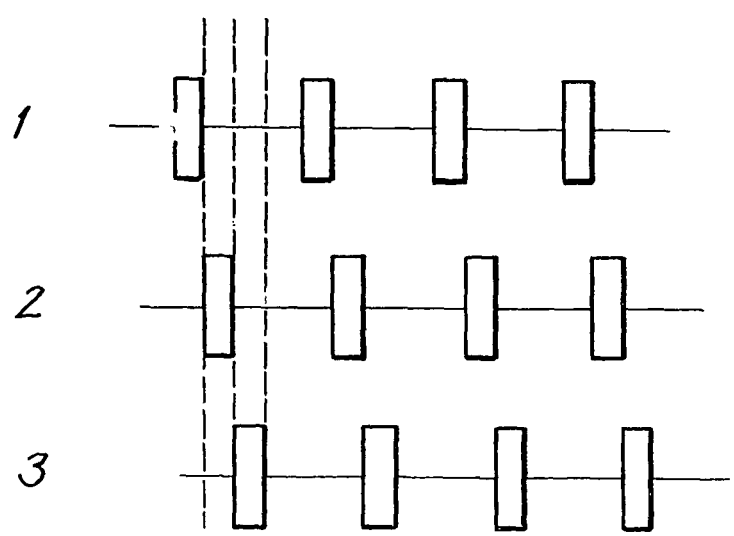
FIG. 6 is another depiction of plasticity informative stimuli as a function of time as output by the apparatus.

In another embodiment, if the stimuli are applied to multiple, if not all, stimulating electrodes, in a sequential mode, the active part of the duty cycle for one stimulating electrode occurs when all other electrodes are in the inactive part of the duty cycle, so at any given time only one stimulating electrode is active (as depicted in FIG. 6).

Figure 7:
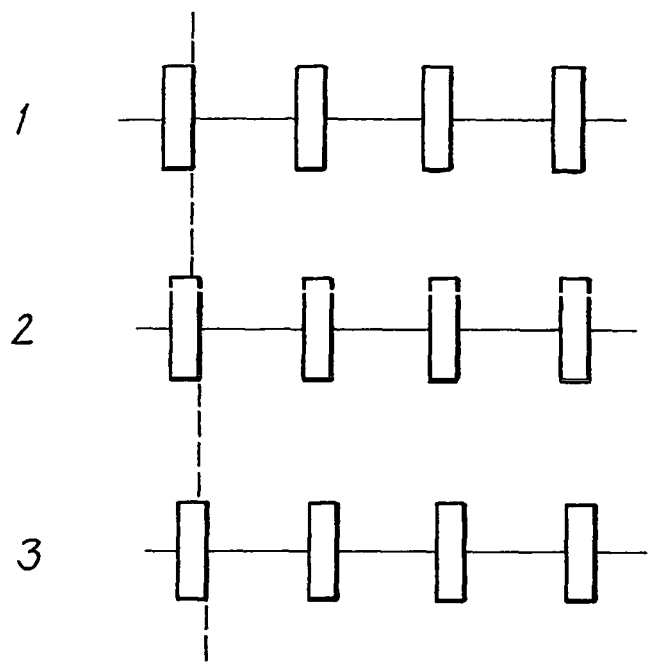
FIG. 7 is another depiction of plasticity informative stimuli as a function of time as output by the apparatus.

Still further, the stimuli can be applied to multiple if not all, stimulating electrodes, in a semi-sequential mode, where the beginning of the active part of the duty cycle for some or all stimulating electrodes is shifted in time so that the stimulation from one electrode occurs with a delay with the respect to other stimulating electrodes, but before the active part of the duty cycle is finished (as is depicted in FIG. 7).

Still further, the plasticity informative stimulation pattern can be a combination of all of the above mentioned modes.

Figure 8:
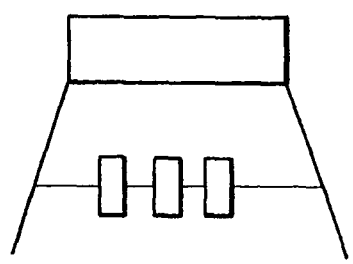
FIG. 8 is another depiction of plasticity informative stimuli as a function of time as output by the apparatus.

In another example, plasticity informative stimuli can be applied sequentially in which multiple duty cycles are delivered through one stimulating electrode before it is applied on another stimulating electrode of the array (as is depicted in FIG. 8).

The plasticity informative stimuli modes, such as those described above, can be delivered according to a predetermined sequence, or be dependent on the activity of the stimulating electrodes carrying the auditory informative stimuli.

In another example, the apparatus measures the activity of one or more of the stimulating electrodes delivering auditory informative stimuli over a period of use, such as a day. For example, the apparatus can measure the frequency of stimulation, the stimulation current, and/or the neural response for each of stimulating electrodes. In this case, the apparatus can measure the different level of activity during the day exhibited by each of the electrodes and so provide a measure of the activity and/or the differences therebetween of the auditory fibres located along the cochlea.

In this case, the plasticity informative stimuli delivered by each electrode of the array can be varied depending on the measure of activity determined for that electrode over the preceding time period. The delivery of the plasticity informative stimuli can be varied such that the overall stimulation received by the auditory fibres from any particular electrode over a predetermined period of time is substantially equal or the same as other auditory fibres receiving stimulation from other electrodes in the array.

In such circumstances, an algorithm may be used to control electrical stimulation carrying plasticity informative stimuli. For any stimulating electrode, $N_0$ delivering auditory informative stimuli, a corresponding weighting function $W_0$ could be calculated according to:

$$W_0 = \Sigma(T_i \times E_i \times N_i), i \text{ being between 1 and } n$$

where n is a total number of stimulating electrodes;

$N_0$ is the stimulating electrode for which weight is being calculated;

$T_i$ is time of stimulus;

$E_i$ is amplitude of stimulus; and $N_i$ is contribution factor for the particular electrode; $N_0$ has the strongest contribution and electrodes positioned further from $N_0$ have decreasing contribution but not necessarily in a uniformly decreasing manner.

In a similar manner, a weighting function Wp for the plasticity informative stimuli can be calculated:

$Wp_0=\Sigma(Tpi \times Epi \times Npi)$, $i$ being between 1 and $n$ where n is a total number of stimulating electrodes;

$N_0$ is the stimulating electrode for which weight is being calculated;

$Tp_i$ is time of stimulus;

$Ep_i$ is amplitude of stimulus; and $Np_i$ is contribution factor for the particular electrode; $N_0$ has the strongest contribution and electrodes positioned further from $N_0$ have decreasing contribution but not necessarily in a uniformly decreasing manner.

In this way, the effect of direct stimulation is taken into account as well as the stimulation delivered by adjoining stimulating electrodes. The "auditory" probability (Pa) for each particular stimulating electrode to deliver plasticity informative stimuli is then a function of the weight (Wi) of auditory informative stimuli, $Pa_i=f(Wi)$. The function that relates the weight of auditory informative stimuli and probability of delivering plasticity informative stimulus is complex.

Further, the "plasticity" probability (Pp) for each particular stimulating electrode to deliver plasticity informative stimuli is then a function of the weight (Wpi) of plasticity informative stimuli, $Pp_i=f(Wpi)$.

The total probability for each particular stimulating electrode to deliver plasticity informative stimuli is then a function of the weight of the auditory and plasticity informative stimuli:

$P=f(Pa,Pp)$

In another embodiment, both auditory and plasticity informative stimuli may be delivered together.

In another embodiment, the auditory informative stimuli is superimposed on the plasticity informative stimuli.

In another embodiment, the system monitors the activity of the electrodes and determines the weight of the auditory informative stimuli, similar to the above formula. The probability of the stimulating electrode delivering plasticity informative stimuli can be inversely proportional to the auditory informative stimuli weight. The result is that the longer the period of time a neuron spends without being active (firing), the higher the probability that that stimulating electrode will deliver plasticity informative stimuli to the auditory system.

The stimulation strategy that delivers plasticity informative stimuli can depend on individual circumstances, such as the speech coding strategy used by the cochlear implant. By applying plasticity informative stimuli, the entire auditory system may be stimulated, so maintaining its plasticity.

The present system may be functional in two modes, ie. acute and chronic. In the acute mode, the plasticity informative stimuli may be delivered to the auditory system over a short period of time when compared to the length of time that the cochlear implant is active. In the chronic mode, the plasticity informative stimuli may be presented over the same or comparable period of time as the length of time that the cochlear implant is active.

The stimulator within the circuitry 44 or housing 22 preferably comprises a processor that processes a set of instructions stored on the processor in the form of software.

The present invention provides a device for delivering stimuli to the neural network of an implantee with the purpose of producing and/or releasing naturally occurring agents, such as BDNF, into the neural network to influence and preferably enhance the neural plasticity thereof.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An apparatus for delivering electrical stimuli to an auditory system of an implantee, comprising:
   an stimulator configured to generate stimulation signals having the stimuli encoded therein; and
   at least one electrode member configured to deliver the stimulation signals to the auditory system;
   wherein the stimuli comprises plasticity informative stimuli having a magnitude below an auditory perception threshold of the implantee, the plasticity informative stimuli configured to facilitate the production and/or release of naturally occurring neurotrophic agents into the auditory system.

2. An apparatus of claim 1 wherein the apparatus is configured to modify the functionality of the auditory system in a predetermined manner.

3. An apparatus of claim 1 wherein the apparatus is configured to deliver the stimuli to at least one of the cochlea, inferior colliculus, the Subthalamic Nucleus (STN), the Globus Pallidus (GPi), and the Thalamus of the implantee.

4. An apparatus of claim 1 wherein the apparatus is a component of a hearing prosthesis that is also adapted to deliver auditory informative stimuli having a magnitude that is about at or above the auditory perception threshold of the implantee to the auditory system of the implantee.

5. An apparatus of claim 4 wherein the hearing prosthesis is a cochlear implant.

6. An apparatus of claim 4 wherein the hearing prosthesis is a hearing aid.

7. An apparatus of claim 4 wherein the prosthesis comprises an electrode array that is implantable in the cochlea of the implantee and is adapted to deliver said plasticity informative stimuli and auditory informative stimuli to the cochlea of the implantee.

8. An apparatus of claim 4 wherein the prosthesis comprises a first electrode array configured to deliver said plasticity informative stimuli and a second electrode array configured to deliver said auditory informative stimuli to the auditory system of the implantee.

9. An apparatus of claim 8 wherein the first electrode array is insertable into the auditory system at a location different from that of the second electrode array.

10. An apparatus of claim 8 wherein both said first and said second electrode arrays comprise an elongate carrier member having a plurality of electrodes mounted thereon.

11. An apparatus of claim 10 wherein the stimulator is electrically connected to each of the elongate carrier members via an electrical lead, the lead including one or more wires extending from each electrode of each elongate member.

12. An apparatus of claim 4 wherein the apparatus is implantable and further wherein the hearing prosthesis comprises an external component that is configured to operate in conjunction with the implantable apparatus, the external component comprising:
    a microphone configured to detect sounds and further configured to output acoustic signals representative of said detected sounds; and
    a processor configured to receive said acoustic signals from the microphone and to convert the signals into stimulation signals representative of the detected sounds, and further configured to encode said stimuli into said stimulation signals, deliver said stimulation signals transcutaneously to the stimulator.

13. An apparatus of claim 12 wherein the external component comprises a controller configured to control the output of the stimulator.

14. An apparatus of claim 12 wherein the external component further comprises a power source.

15. An apparatus of claim 1 wherein the apparatus is configured to deliver said plasticity informative stimuli to the cochlea of the implantee and is configured to operate in conjunction with a cochlear implant device adapted to deliver said auditory informative stimuli to the same cochlea of the implantee.

16. An apparatus of claim 1 wherein the apparatus is configured to operate in conjunction with an external component, the external component comprising a controller configured to control the output of the plasticity informative stimuli from the stimulator.

17. An apparatus of claim 16 wherein the external component further comprises a power source.

18. An apparatus of claim 1 wherein the stimulator is housed in a housing that is totally implantable within the implantee.

19. An apparatus of claim 18 wherein the housing is further configured to house a power source configured to provide the apparatus with at least sufficient power to deliver plasticity informative stimuli.

20. An apparatus of claim 1 wherein said at least one electrode member is part of an electrode array that is implantable in the auditory system of the implantee.

21. An apparatus of claim 20 wherein said electrode array comprises an elongate electrode carrier member having a plurality of electrodes mounted thereon.

22. An apparatus of claim 21 wherein the stimulator is electrically connected to the elongate member by way of an electrical lead, the lead comprising one or more wires extending from each electrode of the array mounted on the elongate member.

23. An apparatus of claim 1 wherein said plasticity informative stimuli is configured to be delivered in a duty cycle comprising a period of time (t1) of active stimulus and a period of time (t2) of no stimulus.

24. An apparatus of claim 23 wherein the apparatus has at least two electrode members and the plasticity informative stimuli is configured to be delivered simultaneously or sequentially by said at least two electrode members.

25. An apparatus of claim 24 wherein the beginning of the active part of the duty cycle for an electrode member is configured to occur with a delay with respect to the commencement of the duty cycle of at least one adjacent electrode member, but before the active part of the duty cycle of said at least one adjacent electrode member is finished.

26. An apparatus of claim 23 wherein the apparatus has at least two electrode members and wherein the active part of the duty cycle for each active electrode is configured to occur simultaneously.

27. An apparatus of claim 23 wherein the apparatus has at least two electrode members and wherein at any given time only one stimulating electrode is active.

28. An apparatus of claim 27 wherein the active part of each duty cycle is configured to be delivered sequentially by said at least two electrode members.

29. An apparatus of claim 1 wherein the apparatus is configured to measure the activity of one or more of the electrode members delivering auditory informative stimuli over a period of time of use.

30. An apparatus of claim 29 wherein the plasticity informative stimuli configured to be delivered by each electrode member is varied depending on the measure of activity determined for that electrode over said period of time.

31. An apparatus of claim 1 wherein the stimulator comprises a processor configured to process a set of instructions stored on the processor in the form of software.

32. An apparatus of claim 1 wherein said naturally occurring neurotrophic agents comprise one or more neurotrophic factors selected from the group comprising Brain Derived Neurotrophic Factor (BDNF), NGF, NT-3, NT-4/5, NT-6, LIF, GDNF, CNTF, and IGF-I.

33. An apparatus of claim 1 wherein said naturally occurring neurotrophic agents comprise neurotrophic factors that increase the survival of spiral ganglion cells.

34. An apparatus of claim 1 wherein said stimuli is configured to elicit outgrowth of spiral ganglion cells towards said at least one electrode member.

35. An apparatus of claim 1 wherein said stimuli is configured to be delivered at a frequency less than 5 kHz.

36. An apparatus of claim 1 wherein the apparatus is configured to deliver plasticity informative stimuli at times when the apparatus is not delivering auditory informative stimuli.

37. A method of delivering stimuli to an auditory system of an implantee, via an stimulator electrically coupled to at least one electrode member, wherein the electrode member is positioned to deliver the stimuli to the implantee, comprising:
generating stimulation signals having the stimuli to be delivered encoded therein; and
delivering said stimulation signals via at least one electrode member to the auditory system of the implantee;
wherein the stimuli comprises plasticity informative stimuli having a magnitude below an auditory perception threshold of the implantee and auditory informative stimuli, the plasticity informative stimuli configured to facilitate the production and/or release of naturally occurring neurotrophic agents into the auditory system.

38. A method of delivering stimuli to the auditory system of claim 37 wherein the stimuli is configured to modify the functionality of the auditory system in a predetermined desired manner.

39. A method of delivering stimuli to the auditory system of claim 37, further comprising:
positioning least one electrode member in a cochlea of the implantee prior to said delivering stimulation signals.

40. A method of delivering stimuli to the auditory system of claim 37 wherein said at least one electrode is adapted to deliver said plasticity informative stimuli and said auditory informative stimuli to the cochlea of the implantee.

41. An implantable apparatus for delivering electrical stimuli to an auditory system of an implantee, the apparatus comprising:
a stimulator configured to generate stimulation signals; and
an electrode array implantable in the auditory system, comprising at least one electrode member configured to deliver the stimulation signals to the auditory system;
wherein the stimuli comprises plasticity informative stimuli having a magnitude below a perception threshold of the implantee, the plasticity informative stimuli configured to facilitate the production and/or release of naturally occurring neurotrophic agents into the auditory system.

42. An implantable apparatus of claim 41 wherein the stimuli is configured to modify the functionality of the auditory system in a predetermined desired manner.

43. An implantable apparatus of claim 41 wherein the apparatus is configured to deliver the stimuli to at least one of the cochlea, inferior colliculus, the Subthalamic Nucleus (STN), the Globus Pallidus (GPi), and the Thalamus of the implantee.

44. An implantable apparatus of claim 41 wherein the perception threshold is an auditory perception threshold of the implantee.

45. An implantable apparatus of claim 41 wherein the apparatus is a component of a hearing prosthesis that is also adapted to deliver auditory informative stimuli having a magnitude that is about at or above the auditory perception threshold of the implantee to the auditory system of the implantee.

46. An implantable apparatus of claim 45 wherein the hearing prosthesis is a cochlear implant.

47. An implantable apparatus of claim 45 wherein the hearing prosthesis is a hearing aid.

48. An implantable apparatus of claim 45 wherein said electrode array is implantable in the cochlea of the implantee and is adapted to deliver said plasticity informative stimuli and said auditory informative stimuli to the cochlea of the implantee.

49. An implantable apparatus of claim 45 wherein the prosthesis comprises a first electrode array configured to deliver plasticity informative stimuli and a second electrode array configured to deliver auditory informative stimuli to the auditory system of the implantee.

50. An implantable apparatus of claim 49 wherein the first electrode array is insertable into the auditory system at a location different from that of the second electrode array.

51. An implantable apparatus of claim 44 wherein the apparatus is configured to deliver plasticity informative stimuli to the cochlea of the implantee and is configured to operate in conjunction with a cochlear implant device adapted to deliver auditory informative stimuli to the same cochlea of the implantee.

52. An implantable apparatus of claim 44 wherein the apparatus is configured to operate in conjunction with an external component, the external component comprising a controller that is configured to control the output of the plasticity informative stimuli from the stimulator.

53. An implantable apparatus of claim 44 wherein the stimulator is housed in a housing that is totally implantable within the implantee.

54. An implantable apparatus of claim 41 wherein the apparatus has at least two electrode members and the plasticity informative stimuli is configured to be delivered simultaneously or sequentially by said at least two electrode members.

55. An implantable apparatus of claim 41 wherein the apparatus has at least two electrode members and wherein the active part of the duty cycle for each active electrode is configured to occur simultaneously.

56. An implantable apparatus of claim 41 wherein the apparatus has at least two electrode members and wherein at any given time only one stimulating electrode is active.

57. An implantable apparatus of claim 41 wherein said naturally occurring neurotrophic agents comprise one or more neurotrophic factors selected from the group comprising Brain Derived Neurotrophic Factor (BDNF), NGF, NT-3, NT-4/5, NT-6, LIF, GDNF, CNTF, and IGF-I.

58. An implantable apparatus of claim 41 wherein said naturally occurring neurotrophic agents comprise neurotrophic factors that increase the survival of spiral ganglion cells.

59. An implantable apparatus of claim 41 wherein said stimuli is configured to elicit outgrowth of spiral ganglion cells towards said at least one electrode member.

60. An implantable apparatus of claim 41 wherein the apparatus is configured to deliver plasticity informative stimuli at times when the apparatus is not delivering auditory informative stimuli.

61. A method of delivering stimuli to an auditory system of an implantee via an electrode array having at least one electrode member, configured to deliver the stimuli to the implantee and positioned in a neural network, comprising:
  generating stimulation signals having the stimuli to be delivered encoded therein; and
  delivering said stimulation signals to said via at least one electrode member to the implantee;
  wherein the stimuli includes plasticity informative stimuli having a magnitude below a perception threshold of the implantee, the plasticity informative stimuli configured to facilitate the production and/or release of naturally occurring neurotrophic agents into the neural network.

62. A method of delivering stimuli to the neural network of claim 61 wherein the stimuli is configured to modify the functionality of the neural network in a predetermined desired manner.

63. A method of delivering stimuli to the neural network of claim 61 wherein the stimuli is configured to be delivered to the auditory system of the implantee.

64. A method of delivering stimuli to the neural network of claim 61 wherein positioning an electrode array comprises positioning said electrode array in a cochlea of the implantee.

65. A method of delivering stimuli to the neural network of claim 61 wherein said at least one electrode is adapted to deliver plasticity informative stimuli and auditory informative stimuli to the cochlea of the implantee.

66. An implantable apparatus for delivering electrical stimuli to a neural network of an implantee, the apparatus comprising:
  a stimulator configured to generate stimulation signals; and
  at least one electrode member configured to receive the stimulation signals and configured to deliver the stimuli to the neural network in response to said signals;
  wherein the stimuli includes plasticity informative stimuli having a magnitude below a perception threshold of the implantee, the plasticity informative stimuli facilitating the production and/or release of naturally occurring neurotrophic agents into the neural network, and
  wherein said naturally occurring neurotrophic agents comprise one or more neurotrophic factors selected from the group comprising Brain Derived Neurotrophic Factor (BDNF), NGF, NT-3, NT-4/5, NT-6, LIF, GDNF, CNTF, and IGF-I.

67. An implantable apparatus of claim 66 wherein the apparatus is configured to deliver stimuli to the auditory system of the implantee.

68. An implantable apparatus of claim 67 wherein the perception threshold is an auditory perception threshold of the implantee.

69. An implantable apparatus of claim 68 wherein the apparatus is a component of a hearing prosthesis that is also adapted to deliver auditory informative stimuli having a magnitude that is about at or above the auditory perception threshold of the implantee to the auditory system of the implantee.

70. An implantable apparatus of claim 69 wherein the hearing prosthesis is a cochlear implant.

71. An implantable apparatus of claim 69 wherein the hearing prosthesis is a hearing aid.

72. An implantable apparatus of claim 69 wherein the prosthesis includes an electrode array that is implantable in the cochlea of the implantee and is adapted to deliver both plasticity informative stimuli and auditory informative stimuli to the cochlea of the implantee.

73. An implantable apparatus of claim 69 wherein the prosthesis comprises a first electrode array configured to deliver plasticity informative stimuli and a second electrode array configured to deliver auditory informative stimuli to the auditory system of the implantee.

74. An implantable apparatus of claim 68 wherein the apparatus delivers plasticity informative stimuli to the cochlea of the implantee and is configured to operate in conjunction with a cochlear implant device adapted to deliver auditory informative stimuli to the same cochlea of the implantee.

75. An implantable apparatus of claim 66 wherein the apparatus is configured to deliver the stimuli to at least one of the cochlea, inferior colliculus, the Subthalamic Nucleus (STN), the Globus Pallidus (GPi), and the Thalamus of the implantee.

76. An implantable apparatus of claim 75 wherein said naturally occurring neurotrophic agents comprise neurotrophic factors that increase the survival of spiral ganglion cells.

77. An implantable apparatus of claim 66 wherein the apparatus has at least two electrode members and the plasticity informative stimuli is configured to be delivered simultaneously or sequentially by said at least two electrode members.

78. An implantable apparatus of claim 66 wherein the apparatus has at least two electrode members and wherein at any given time only one stimulating electrode is active.

79. An implantable apparatus of claim 66 wherein said stimuli elicits outgrowth of spiral ganglion cells towards said at least one electrode member.

80. A method of delivering stimuli to an auditory system of an implantee, via an stimulator electrically coupled to at least one electrode member, wherein the electrode member is positioned to deliver the stimuli to the implantee, comprising the steps of:
   generating stimulation signals having the stimuli to be delivered encoded therein; and
   delivering said stimulation signals via at least one electrode member to the auditory system of the implantee;
   wherein the stimuli includes plasticity informative stimuli having a magnitude below a perception threshold of the implantee, the plasticity informative stimuli facilitating the production and/or release of naturally occurring neurotrophic agents into the auditory system, wherein said naturally occurring neurotrophic agents comprise one or more neurotrophic factors selected from the group comprising Brain Derived Neurotrophic Factor (BDNF), NGF, NT-3, NT-4/5, NT-6, LIF, GDNF, CNTF, and IGF-I.

81. A method of delivering stimuli to the auditory system of claim 80 wherein the stimuli is configured to be delivered to the auditory system of the implantee.

82. A method of delivering stimuli to the auditory system of claim 80 wherein positioning at least one electrode member comprises positioning said at least one electrode member in a cochlea of the implantee.

83. A method of delivering stimuli to the auditory system of claim 80 wherein said at least one electrode is adapted to deliver plasticity informative stimuli and auditory informative stimuli to the cochlea of the implantee.

84. An implantable apparatus for delivering electrical stimuli to a neural network of an implantee, the apparatus comprising:
   a stimulator that generates stimulation signals; and
   at least one electrode member configured to receive the stimulation signals and configured to deliver the stimuli to the neural network in response to said signals;
   wherein the stimuli includes plasticity informative stimuli having a magnitude below a perception threshold of the implantee, the plasticity informative stimuli facilitating the production and/or release of naturally occurring neurotrophic agents into the neural network, and
   wherein said naturally occurring neurotrophic agents comprise neurotrophic factors that increase the survival of spiral ganglion cells.

85. An implantable apparatus of claim 84 wherein the apparatus delivers stimuli to the auditory system of the implantee.

86. An implantable apparatus of claim 85 wherein the perception threshold is an auditory perception threshold of the implantee.

87. An implantable apparatus of claim 86 wherein the apparatus is a component of a hearing prosthesis that is also adapted to deliver auditory informative stimuli having a magnitude that is about at or above the auditory perception threshold of the implantee to the auditory system of the implantee.

88. An implantable apparatus of claim 87 wherein the hearing prosthesis is a cochlear implant.

89. An implantable apparatus of claim 87 wherein the hearing prosthesis is a hearing aid.

90. An implantable apparatus of claim 86 wherein the apparatus delivers plasticity informative stimuli to the cochlea of the implantee and is configured to operate in conjunction with a cochlear implant device adapted to deliver auditory informative stimuli to the same cochlea of the implantee.

91. An implantable apparatus of claim 86 wherein the apparatus is configured to operate in conjunction with an external component, the external component comprising a controller that controls the output of the plasticity informative stimuli from the stimulator.

92. An implantable apparatus of claim 84 wherein the apparatus is configured to deliver the stimuli to at least one of the cochlea, inferior colliculus, the Subthalamic Nucleus (STN), the Globus Pallidus (GPi), and the Thalamus of the implantee.

93. An implantable apparatus of claim 84 wherein the apparatus has at least two electrode members and the plasticity informative stimuli is configured to be delivered simultaneously or sequentially by said at least two electrode members.

94. An implantable apparatus of claim 84 wherein the apparatus has at least two electrode members and wherein the active part of the duty cycle for each active electrode occurs simultaneously.

95. An implantable apparatus of claim 84 wherein the apparatus has at least two electrode members and wherein at any given time only one stimulating electrode is active.

96. An implantable apparatus of claim 84 wherein said naturally occurring neurotrophic agents comprise one or more neurotrophic factors selected from the group comprising Brain Derived Neurotrophic Factor (BDNF), NGF, NT-3, NT-4/5, NT-6, LIF, GDNF, CNTF, and IGF-I.

97. An implantable apparatus of claim 84 wherein said stimuli elicits outgrowth of spiral ganglion cells towards said at least one electrode member.

98. A method of delivering stimuli to an auditory system of an implantee, via an stimulator electrically coupled to at least one electrode member, wherein the electrode member is positioned to deliver the stimuli to the implantee, comprising the steps of:

generating stimulation signals having the stimuli to be delivered encoded therein; and delivering said stimulation signals via at least one electrode member to the implantee;

wherein the stimuli includes plasticity informative stimuli having a magnitude below a perception threshold of the implantee, the plasticity informative stimuli facilitating the production and/or release of naturally occurring neurotrophic agents into the auditory system, wherein said naturally occurring agents comprise neurotrophic factors that increase the survival of spiral ganglion cells.

99. A method of delivering stimuli to the auditory system of claim 98 wherein the stimuli is configured to be delivered to the auditory system of the implantee.

100. A method of delivering stimuli to the auditory system of claim 98 wherein positioning at least one electrode member comprises positioning said at least one electrode member in a cochlea of the implantee.

101. A method of delivering stimuli to the auditory system of claim 98 wherein said at least one electrode is adapted to deliver plasticity informative stimuli and auditory informative stimuli to the cochlea of the implantee.

102. An implantable apparatus for delivering electrical stimuli to a neural network of an implantee, the apparatus comprising:

a stimulator that generates stimulation signals; and at least one electrode member configured to receive the stimulation signals and configured to deliver the stimuli to the neural network in response to said signals;

wherein the stimuli includes plasticity informative stimuli having a magnitude below a perception threshold of the implantee, the plasticity informative stimuli facilitating the production and/or release of naturally occurring neurotrophic agents into the neural network, and wherein said stimuli elicits outgrowth of spiral ganglion cells towards said at least one electrode member.

103. An implantable apparatus of claim 102 wherein the apparatus delivers stimuli to the auditory system of the implantee.

104. An implantable apparatus of claim 103 wherein the perception threshold is an auditory perception threshold of the implantee.

105. An implantable apparatus of claim 102 wherein the wherein the apparatus is configured to deliver the stimuli to at least one of the cochlea, inferior colliculus, the Subthalamic Nucleus (STN), the Globus Pallidus (GPi), and the Thalamus of the implantee.

106. An implantable apparatus of claim 102 wherein the hearing prosthesis is a cochlear implant.

107. An implantable apparatus of claim 102 wherein the hearing prosthesis is a hearing aid.

108. An implantable apparatus of claim 102 wherein the apparatus has at least two electrode members and the plasticity informative stimuli is configured to be delivered simultaneously or sequentially by said at least two electrode members.

109. An implantable apparatus of claim 102 wherein the apparatus has at least two electrode members and wherein at any given time only one stimulating electrode is active.

110. An implantable apparatus of claim 102 wherein said naturally occurring neurotrophic agents comprise one or more neurotrophic factors selected from the group comprising Brain Derived Neurotrophic Factor (BDNF), NGF, NT-3, NT-4/5, NT-6, LIF, GDNF, CNTF, and IGF-I.

111. An implantable apparatus of claim 102 wherein said naturally occurring neurotrophic agents comprise neurotrophic factors that increase the survival of spiral ganglion cells.

112. A method of delivering stimuli to an auditory system of an implantee, via an stimulator electrically coupled to at least one electrode member, wherein the electrode member is positioned to deliver the stimuli to the implantee, comprising the steps of:

generating stimulation signals having the stimuli to be delivered encoded therein; and delivering said stimulation signals via at least one electrode member to the implantee;

wherein the stimuli includes plasticity informative stimuli having a magnitude below a perception threshold of the implantee, the plasticity informative stimuli facilitating the production and/or release of naturally occurring neurotrophic agents into the auditory system, wherein said stimuli elicits outgrowth of spiral ganglion cells.

113. A method of delivering stimuli to a neural network of claim 112 wherein the stimuli provided by the stimulation signals is configured to be delivered to the auditory system of the implantee.

* * * * *